United States Patent
Ebbehøj et al.

(10) Patent No.: US 7,544,657 B2
(45) Date of Patent: Jun. 9, 2009

(54) STABILIZED EXENDIN-4 COMPOUNDS

(75) Inventors: Kirsten Ebbehøj, Nærum (DK); Trine Jepsen, Copenhagen (DK); Carsten Boye Knudsen, Greve (DK); Bjarne Due Larsen, Roskilde (DK); David Knott, Hertford (DK)

(73) Assignee: Zealand Pharma A/S, Glostrup (DK)

( * ) Notice: Subject to any disclaimer, the term of this patent is extended or adjusted under 35 U.S.C. 154(b) by 34 days.

(21) Appl. No.: 10/529,858

(22) PCT Filed: Oct. 2, 2003

(86) PCT No.: PCT/DK03/00651

§ 371 (c)(1),
(2), (4) Date: Apr. 26, 2006

(87) PCT Pub. No.: WO2004/035623

PCT Pub. Date: Apr. 29, 2004

(65) Prior Publication Data

US 2006/0194719 A1    Aug. 31, 2006

Related U.S. Application Data

(60) Provisional application No. 60/415,626, filed on Oct. 2, 2002.

(51) Int. Cl.
*A61K 38/00* (2006.01)
(52) U.S. Cl. .............. 514/12; 514/2; 530/300; 530/308; 530/324
(58) Field of Classification Search ........... None
See application file for complete search history.

(56) References Cited

U.S. PATENT DOCUMENTS

| | | | |
|---|---|---|---|
| 5,407,609 | A | 4/1995 | Tice et al. |
| 5,424,286 | A | 6/1995 | Eng |
| 5,545,618 | A | 8/1996 | Buckley et al. |
| 5,614,492 | A | 3/1997 | Habener |
| 5,631,224 | A | 5/1997 | Efendic et al. |
| 5,654,008 | A | 8/1997 | Herbert et al. |
| 5,670,360 | A | 9/1997 | Thorens |
| 5,846,747 | A | 12/1998 | Thorens et al. |
| 5,846,937 | A | 12/1998 | Drucker |
| 6,006,753 | A | 12/1999 | Efendic |
| 6,051,689 | A | 4/2000 | Thorens |
| 6,110,703 | A | 8/2000 | Egel-Mitani et al. |
| 6,191,102 | B1 | 2/2001 | DiMarchi et al. |
| 6,268,343 | B1 | 7/2001 | Knudsen et al. |
| 6,271,241 | B1 | 8/2001 | DiSimone et al. |
| 6,277,819 | B1 | 8/2001 | Efendic |
| 6,284,725 | B1 | 9/2001 | Coolidge et al. |
| 6,329,336 | B1 | 12/2001 | Bridon et al. |
| 6,344,180 | B1 | 2/2002 | Holst et al. |
| 6,358,924 | B1 | 3/2002 | Hoffmann |
| 6,384,016 | B1 | 5/2002 | Kaarsholm |
| 6,388,053 | B1 | 5/2002 | Galloway et al. |
| 6,410,508 | B1 | 6/2002 | Isales et al. |
| 6,528,486 | B1 | 3/2003 | Larsen et al. |
| 2004/0106547 | A1 | 6/2004 | Larsen et al. |
| 2007/0111940 | A1 | 5/2007 | Larsen et al. |

FOREIGN PATENT DOCUMENTS

| | | |
|---|---|---|
| DE | 19637230 | 3/1998 |
| WO | WO9318786 | 9/1993 |
| WO | WO9805351 | 2/1998 |
| WO | WO9808531 | 3/1998 |
| WO | WO9808873 | 3/1998 |
| WO | WO9819698 | 5/1998 |
| WO | WO9830231 | 7/1998 |
| WO | WO9835033 | 8/1998 |
| WO | WO9839022 | 9/1998 |
| WO | WO9907404 | 2/1999 |
| WO | WO9925727 | 5/1999 |
| WO | WO9925728 | 5/1999 |
| WO | WO9940788 | 8/1999 |
| WO | WO9943708 | 9/1999 |
| WO | WO9946283 | 9/1999 |
| WO | WO0066629 | 11/2000 |
| WO | WO0104156 | 1/2001 |

OTHER PUBLICATIONS

Goke et al., J. Biol. Chem. 1993, 268, 19650-19655.*
Byrne et al., "Inhibitory Effects of Hyperglycaemia on Fed Jejunal Motility: Potential Role of Hyperinsulinaemia," *Euro. J. Clin. Invest.* 28:72-78 (1998).
Chen et al., "Tissue-specific Expression of Unique mRNAs That Encode Proglucagon-derived Peptides or Exendin 4 in the Lizard," *J. Biol. Chem.* 272:4108-4115 (1997).
D'Alessio et al., "Glucagon-like Peptide 1 Enhances Glucose Tolerance Both by Stimulation of Insulin Release and by Increasing Insulin-independent Glucose Disposal," *J. Clin. Invest.* 93:2263-2266 (1994).
Drucker, D., "Glucagon-Like Peptides," *Diabetes* 47:159-169 (1998).

(Continued)

*Primary Examiner*—Robert Landsman
*Assistant Examiner*—Gyan Chandra
(74) *Attorney, Agent, or Firm*—Kristina Bieker-Brady; Clark & Elbing LLP

(57) ABSTRACT

The present invention disclosed compositions comprising a stabilized Exendin-4 (1-39) and related compounds. The invention describes stabilized Exendin-4 agonists that include at least one modified amino acid residue particularly at positions Gln13, Met14, Trp25, or Asn28 of the Exendin-4 (1-39) molecule. Disclosed are preferred modifications of deaminated, hydrolyzed, oxidized, or isomerized reaction products of the specified amino acid residues corresponding to the same positions in the Exendin-4 molecule. The invention also relates to methods of making and using the stabilized Exendin compounds, such as for the treatment of diabetes.

32 Claims, 7 Drawing Sheets

OTHER PUBLICATIONS

Drucker, D., "Minireview: The Glucagon-Like Peptides," *Endocrinology* 521-527. (2001).

Göke et al., "Exendin-4 is a High Potency Agonist and Truncated Exendin-(9-39)-amide an Antagonist at the Glucagon-like Peptide 1-(7-36)-amide Receptor of Insulin-secreting β-Cells," *J. Biol. Chem.* 268:19650-19655 (1993).

Greig et al., "Once Daily Injection of Exendin-4 to Diabetic Mice Achieves Long-Term Beneficial Effects on Blood Glucose Concentrations." *Diabetologia* 42:45-50 (1999).

Merrifield, B., "Solid Phase Synthesis." *Science* 232:341-347 (1986).

Nauck et al., "Glucagon-Like Peptide 1 and its Potential in the Treatment of Non-Insulin-Dependent Diaetes Mellitus," *Horm. Metab. Res.* 29:411-416 (1997).

Needleman et al., "A General Method Applicable to the Search for Similarities in the Amino Acid Sequence of Two Proteins," *J. Mol. Biol.* 48:443-453 (1970).

Ørskov, C., "Glucagon-like Peptide-1, a New Hormone of the Enteroinsular Axis," *Diabetologia* 35:701-711 (1992).

Pederson et al., "Improved Glucose Tolerance in Zucker Fatty Rats by Oral Administration of the Dipeptidyl Peptidase IV Inhibitor Isoleucine Thiazolidide." *Diabetes* 47:1253-1258 (1998).

Pohl et al., "Molecular Cloning of the Heloderman and Exendin-4 cDNAs in the Lizard," *J. Biol. Chem.* 273:9778-9784 (1998).

International Search Report from PCT/DK03/00651 dated Oct. 2, 2003.

International Preliminary Examination Report from PCT/DK03/00651 dated Jan. 31, 2005.

* cited by examiner

Effect of Compound 1 on glucose tolerance in *db/db* mice

Effect of Compound 14 on glucose tolerance in *db/db* mice

Effect of Compound 6 on glucose tolerance in *db/db* mice

Effect of Compound 7 on glucose tolerance in *db/db* mice

Effect of Compound 2 on glucose tolerance in *db/db* mice

Effect of Compound 1-5 on Oral Glucose Tolerance in *db/db* mice

Figure 9

Compound 1

H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-$NH_2$

Compound 2

H-His-Gly-Glu-Gly-Thr-Phe-Thr-Ser-Asp-Leu-Ser-Lys-Gln-Met(O)-Glu-Glu-Glu-Ala-Val-Arg-Leu-Phe-Ile-Glu-Trp-Leu-Lys-αAsp-Gly-Gly-Pro-Ser-Ser-Gly-Ala-Pro-Pro-Ser-Lys-Lys-Lys-Lys-Lys-Lys-$NH_2$

Compound 3

H-His-Gly-Glu-Gly-Thr-Phe-Thr-Ser-Asp-Leu-Ser-Lys-Gln-Met(O)-Glu-Glu-Glu-Ala-Val-Arg-Leu-Phe-Ile-Glu-Trp($O_2$)-Leu-Lys-IsoAsp-Gly-Gly-Pro-Ser-Ser-Gly-Ala-Pro-Pro-Ser-Lys-Lys-Lys-Lys-Lys-Lys-$NH_2$

Compound 4

H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp($O_2$)-Leu-Lys-Cyclic-Imide-Gly-Gly-Pro-Ser-Ser-Gly-Ala-Pro-Pro-Ser-Lys-Lys-Lys-Lys-Lys-Lys-$NH_2$

Compound 5

H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asp-Gly-Gly-Pro-Ser-Ser-Gly-Ala-Pro-Pro-Ser-Lys-Lys-Lys-Lys-Lys-Lys-$NH_2$

Compound 6

H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-IsoAsp-Gly-Gly-Pro-Ser-Ser-Gly-Ala-Pro-Pro-Ser-Lys-Lys-Lys-Lys-Lys-Lys-$NH_2$

Compound 7

H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Cyclic-Imide-Gly-Gly-Pro-Ser-Ser-Gly-Ala-Pro-Pro-Ser-Lys-Lys-Lys-Lys-Lys-Lys-$NH_2$

Compound 8

H-His-Gly-Glu-Gly-Thr-Phe-Thr-Ser-Asp-Leu-Ser-Lys-Glu-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-$NH_2$

Figure 9 con't.

Compound 9

H-His-Gly-Glu-Gly-Thr-Phe-Thr-Ser-Asp-Leu-Ser-Lys-Glu-Met-Glu-Glu-Glu-Ala-Val-Arg-Leu-Phe-Ile-Glu-Trp-Leu-Lys-Asp-Gly-Gly-Pro-Ser-Ser-Gly-Ala-Pro-Pro-Pro-Ser-$NH_2$

Compound 10

H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asp-Gly-Gly-Pro-Ser-Ser-Gly-Ala-Pro-Pro-Pro-Ser-$NH_2$

Compound 11

H-His-Gly-Glu-Gly-Thr-Phe-Thr-Ser-Asp-Leu-Ser-Lys-Glu-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-$NH_2$

Compound 12

H-His-Gly-Glu-Gly-Thr-Phe-Thr-Ser-Asp-Leu-Ser-Lys-Gln-Met(O)-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-$NH_2$

Compound 13

H-His-Gly-Glu-Gly-Thr-Phe-Thr-Ser-Asp-Leu-Ser-Lys-Gln-Met($O_2$)-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-$NH_2$

Compound 14

H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-D-IsoAsp-Gly-Gly-Pro-Ser-Ser-Gly-Ala-Pro-Pro-Ser-Lys-Lys-Lys-Lys-Lys-Lys-$NH_2$

SEQUENCE LISTING

```
<160> NUMBER OF SEQ ID NOS: 108

<210> SEQ ID NO 1
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 2
<211> LENGTH: 44
<212> TYPE: PRT
<213> ORGANISM: Artificial Sequence
```

-continued

```
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Met(O)
<220> FEATURE:
<221> NAME/KEY: MOD_RES
<222> LOCATION: (28)..(28)
<223> OTHER INFORMATION: alpha-Asp

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser Lys Lys Lys Lys Lys Lys
            35                  40

<210> SEQ ID NO 3
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Met(O)
<220> FEATURE:
<221> NAME/KEY: MOD_RES
<222> LOCATION: (25)..(25)
<223> OTHER INFORMATION: Trp(O2)
<220> FEATURE:
<221> NAME/KEY: MOD_RES
<222> LOCATION: (28)..(28)
<223> OTHER INFORMATION: IsoAsp

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser Lys Lys Lys Lys Lys Lys
            35                  40

<210> SEQ ID NO 4
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Trp(O2)
<220> FEATURE:
<221> NAME/KEY: MOD_RES
<222> LOCATION: (28)..(28)
<223> OTHER INFORMATION: Cyclic Imide

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Xaa Gly Gly Pro Ser
            20                  25                  30
```

```
Ser Gly Ala Pro Pro Ser Lys Lys Lys Lys Lys Lys
        35                  40

<210> SEQ ID NO 5
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser Lys Lys Lys Lys Lys Lys
        35                  40

<210> SEQ ID NO 6
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(28)
<223> OTHER INFORMATION: IsoAsp

<400> SEQUENCE: 6

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser Lys Lys Lys Lys Lys Lys
        35                  40

<210> SEQ ID NO 7
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(28)
<223> OTHER INFORMATION: Cyclic Imide

<400> SEQUENCE: 7

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Xaa Gly Gly Pro Ser
            20                  25                  30

Ser Gly Ala Pro Pro Ser Lys Lys Lys Lys Lys Lys
        35                  40

<210> SEQ ID NO 8
<211> LENGTH: 39
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 8

His Gly Glu Gly Thr Phe Thr Ser Asp Leu Ser Lys Glu Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 9
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

His Gly Glu Gly Thr Phe Thr Ser Asp Leu Ser Lys Glu Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Pro Ser
        35

<210> SEQ ID NO 10
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Pro Ser
        35

<210> SEQ ID NO 11
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

His Gly Glu Gly Thr Phe Thr Ser Asp Leu Ser Lys Glu Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 12
<211> LENGTH: 44
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Met(O)

<400> SEQUENCE: 12

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 13
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Met(O)

<400> SEQUENCE: 13

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 14
<211> LENGTH: 44
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(28)
<223> OTHER INFORMATION: D-IsoAsp

<400> SEQUENCE: 14

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser Lys Lys Lys Lys Lys Lys
        35                  40

<210> SEQ ID NO 15
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

His Gly Glu Gly Thr Phe Thr Ser Asp Leu Ser Lys Gln Met Glu Glu
1               5                   10                  15
```

```
Glu Ala Val Arg Leu Phe Ile Glu Trp Leu Lys Asp Gly Gly Pro Ser
            20                  25                  30

Ser Gly Ala Pro Pro Ser
        35

<210> SEQ ID NO 16
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(28)
<223> OTHER INFORMATION: IsoAsp

<400> SEQUENCE: 16

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser
        35

<210> SEQ ID NO 17
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(28)
<223> OTHER INFORMATION: Cyclic Imide

<400> SEQUENCE: 17

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Xaa Gly Gly Pro Ser
            20                  25                  30

Ser Gly Ala Pro Pro Ser
        35

<210> SEQ ID NO 18
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Met(O)

<400> SEQUENCE: 18

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35
```

```
<210> SEQ ID NO 19
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Trp(O2)

<400> SEQUENCE: 19

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 20
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Met(O)

<400> SEQUENCE: 20

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser
        35

<210> SEQ ID NO 21
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Met(O)
<220> FEATURE:
<221> NAME/KEY: MOD_RES
<222> LOCATION: (28)..(28)
<223> OTHER INFORMATION: IsoAsp

<400> SEQUENCE: 21

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser
        35

<210> SEQ ID NO 22
<211> LENGTH: 38
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Met(O)
<220> FEATURE:
<221> NAME/KEY: MOD_RES
<222> LOCATION: (28)..(28)
<223> OTHER INFORMATION: Cyclic Imide

<400> SEQUENCE: 22

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Xaa Gly Gly Pro Ser
            20                  25                  30

Ser Gly Ala Pro Pro Ser
        35

<210> SEQ ID NO 23
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Met(O)
<220> FEATURE:
<221> NAME/KEY: MOD_RES
<222> LOCATION: (25)..(25)
<223> OTHER INFORMATION: Trp(O2)

<400> SEQUENCE: 23

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 24
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Met(O)
<220> FEATURE:
<221> NAME/KEY: MOD_RES
<222> LOCATION: (25)..(25)
<223> OTHER INFORMATION: Trp(O2)

<400> SEQUENCE: 24

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser
```

<210> SEQ ID NO 25
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Met(O)
<220> FEATURE:
<221> NAME/KEY: MOD_RES
<222> LOCATION: (25)..(25)
<223> OTHER INFORMATION: Trp(O2)
<220> FEATURE:
<221> NAME/KEY: MOD_RES
<222> LOCATION: (28)..(28)
<223> OTHER INFORMATION: IsoAsp

<400> SEQUENCE: 25

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser
        35

<210> SEQ ID NO 26
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Met(O)
<220> FEATURE:
<221> NAME/KEY: MOD_RES
<222> LOCATION: (25)..(25)
<223> OTHER INFORMATION: Trp(O2)
<220> FEATURE:
<221> NAME/KEY: MOD_RES
<222> LOCATION: (28)..(28)
<223> OTHER INFORMATION: Cyclic Imide

<400> SEQUENCE: 26

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Xaa Gly Gly Pro Ser
            20                  25                  30

Ser Gly Ala Pro Pro Ser
        35

<210> SEQ ID NO 27
<211> LENGTH: 50
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 28
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Ser
        35

<210> SEQ ID NO 29
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Ser
        35                  40

<210> SEQ ID NO 30
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Ser
        35                  40

<210> SEQ ID NO 31
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 31

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Ser Lys Lys Lys Lys Lys Lys
        35                  40

<210> SEQ ID NO 32
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Ser Lys Lys Lys Lys Lys Lys
            35                  40                  45

<210> SEQ ID NO 33
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Ser Lys Lys Lys Lys Lys Lys
            35                  40                  45

<210> SEQ ID NO 34
<211> LENGTH: 50
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (34)..(34)
<223> OTHER INFORMATION: Cyclic Imide

<400> SEQUENCE: 34

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Xaa Gly Gly Pro Ser Ser Gly Ala Pro Pro Ser Lys Lys Lys Lys
            35                  40                  45

Lys Lys
    50
```

```
<210> SEQ ID NO 35
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(28)
<223> OTHER INFORMATION: Cyclic Imide

<400> SEQUENCE: 35

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Xaa Gly Gly Pro Ser
            20                  25                  30

Ser Gly Ala Ser
        35

<210> SEQ ID NO 36
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (34)..(34)
<223> OTHER INFORMATION: Cyclic Imide

<400> SEQUENCE: 36

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Xaa Gly Gly Pro Ser Ser Gly Ala Ser
        35                  40

<210> SEQ ID NO 37
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (34)..(34)
<223> OTHER INFORMATION: Cyclic Imide

<400> SEQUENCE: 37

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Xaa Gly Gly Pro Ser Ser Gly Ala Ser
        35                  40

<210> SEQ ID NO 38
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (28)..(28)
<223> OTHER INFORMATION: Cyclic Imide

<400> SEQUENCE: 38

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Xaa Gly Gly Pro Ser
            20                  25                  30

Ser Gly Ala Ser Lys Lys Lys Lys Lys Lys
        35                  40

<210> SEQ ID NO 39
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (34)..(34)
<223> OTHER INFORMATION: Cyclic Imide

<400> SEQUENCE: 39

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Xaa Gly Gly Pro Ser Ser Gly Ala Ser Lys Lys Lys Lys Lys Lys
        35                  40                  45

<210> SEQ ID NO 40
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (34)..(34)
<223> OTHER INFORMATION: Cyclic Imide

<400> SEQUENCE: 40

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Xaa Gly Gly Pro Ser Ser Gly Ala Ser Lys Lys Lys Lys Lys Lys
        35                  40                  45

<210> SEQ ID NO 41
<211> LENGTH: 50
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (31)..(31)
<223> OTHER INFORMATION: Trp(O2)

<400> SEQUENCE: 41
```

```
Lys Lys Lys Lys Lys Lys His Gly Glu Gly Thr Phe Thr Ser Asp Leu
1               5                   10                  15

Ser Lys Gln Met Glu Glu Ala Val Arg Leu Phe Ile Glu Trp Leu
                20                  25                  30

Lys Asp Gly Gly Pro Ser Ser Gly Ala Pro Pro Ser Lys Lys Lys
            35                  40                  45

Lys Lys
    50
```

<210> SEQ ID NO 42
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Trp(O2)

<400> SEQUENCE: 42

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
                20                  25                  30

Ser Gly Ala Ser
        35
```

<210> SEQ ID NO 43
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (31)..(31)
<223> OTHER INFORMATION: Trp(O2)

<400> SEQUENCE: 43

```
Lys Lys Lys Lys Lys Lys His Gly Glu Gly Thr Phe Thr Ser Asp Leu
1               5                   10                  15

Ser Lys Gln Met Glu Glu Ala Val Arg Leu Phe Ile Glu Trp Leu
                20                  25                  30

Lys Asp Gly Gly Pro Ser Ser Gly Ala Ser
            35                  40
```

<210> SEQ ID NO 44
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (31)..(31)
<223> OTHER INFORMATION: Trp(O2)

<400> SEQUENCE: 44

```
Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
```

-continued

```
                    20                  25                  30

Lys Asp Gly Gly Pro Ser Ser Gly Ala Ser
        35                  40

<210> SEQ ID NO 45
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Trp(O2)

<400> SEQUENCE: 45

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
                20                  25                  30

Ser Gly Ala Ser Lys Lys Lys Lys Lys Lys
        35                  40

<210> SEQ ID NO 46
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (31)..(31)
<223> OTHER INFORMATION: Trp(O2)

<400> SEQUENCE: 46

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
                20                  25                  30

Lys Asp Gly Gly Pro Ser Ser Gly Ala Ser Lys Lys Lys Lys Lys Lys
        35                  40                  45

<210> SEQ ID NO 47
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (31)..(31)
<223> OTHER INFORMATION: Trp(O2)

<400> SEQUENCE: 47

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
                20                  25                  30

Lys Asp Gly Gly Pro Ser Ser Gly Ala Ser Lys Lys Lys Lys Lys Lys
        35                  40                  45

<210> SEQ ID NO 48
```

```
<211> LENGTH: 50
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (31)..(31)
<223> OTHER INFORMATION: Trp(O2)
<220> FEATURE:
<221> NAME/KEY: MOD_RES
<222> LOCATION: (34)..(34)
<223> OTHER INFORMATION: Cyclic Imide

<400> SEQUENCE: 48

Lys Lys Lys Lys Lys Lys His Gly Glu Gly Thr Phe Thr Ser Asp Leu
1               5                   10                  15

Ser Lys Gln Met Glu Glu Ala Val Arg Leu Phe Ile Glu Trp Leu
                20                  25                  30

Lys Xaa Gly Gly Pro Ser Ser Gly Ala Pro Pro Ser Lys Lys Lys
        35                  40                  45

Lys Lys
    50

<210> SEQ ID NO 49
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Trp(O2)
<220> FEATURE:
<221> NAME/KEY: MOD_RES
<222> LOCATION: (28)..(28)
<223> OTHER INFORMATION: Cyclic Imide

<400> SEQUENCE: 49

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Xaa Gly Gly Pro Ser
                20                  25                  30

Ser Gly Ala Ser
        35

<210> SEQ ID NO 50
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (31)..(31)
<223> OTHER INFORMATION: Trp(O2)
<220> FEATURE:
<221> NAME/KEY: MOD_RES
<222> LOCATION: (34)..(34)
<223> OTHER INFORMATION: Cyclic Imide

<400> SEQUENCE: 50

Lys Lys Lys Lys Lys Lys His Gly Glu Gly Thr Phe Thr Ser Asp Leu
1               5                   10                  15
```

```
Ser Lys Gln Met Glu Glu Glu Ala Val Arg Leu Phe Ile Glu Trp Leu
            20                  25                  30

Lys Xaa Gly Gly Pro Ser Ser Gly Ala Ser
        35                  40

<210> SEQ ID NO 51
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (31)..(31)
<223> OTHER INFORMATION: Trp(O2)
<220> FEATURE:
<221> NAME/KEY: MOD_RES
<222> LOCATION: (34)..(34)
<223> OTHER INFORMATION: Cyclic Imide

<400> SEQUENCE: 51

Asn Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Xaa Gly Gly Pro Ser Ser Gly Ala Ser
        35                  40

<210> SEQ ID NO 52
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Trp(O2)
<220> FEATURE:
<221> NAME/KEY: MOD_RES
<222> LOCATION: (28)..(28)
<223> OTHER INFORMATION: Cyclic Imide

<400> SEQUENCE: 52

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Xaa Gly Gly Pro Ser
            20                  25                  30

Ser Gly Ala Ser Lys Lys Lys Lys Lys Lys
        35                  40

<210> SEQ ID NO 53
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (31)..(31)
<223> OTHER INFORMATION: Trp(O2)
<220> FEATURE:
<221> NAME/KEY: MOD_RES
<222> LOCATION: (34)..(34)
<223> OTHER INFORMATION: Cyclic Imide
```

-continued

```
<400> SEQUENCE: 53

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Xaa Gly Gly Pro Ser Ser Gly Ala Ser Lys Lys Lys Lys Lys
        35                  40                  45

<210> SEQ ID NO 54
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (31)..(31)
<223> OTHER INFORMATION: Trp(O2)
<220> FEATURE:
<221> NAME/KEY: MOD_RES
<222> LOCATION: (34)..(34)
<223> OTHER INFORMATION: Cyclic Imide

<400> SEQUENCE: 54

Asn Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Xaa Gly Gly Pro Ser Ser Gly Ala Ser Lys Lys Lys Lys Lys
        35                  40                  45

<210> SEQ ID NO 55
<211> LENGTH: 50
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Met(O)

<400> SEQUENCE: 55

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 56
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Met(O)
```

```
<400> SEQUENCE: 56

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Ser
        35

<210> SEQ ID NO 57
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Met(O)

<400> SEQUENCE: 57

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Ser
        35                  40

<210> SEQ ID NO 58
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Met(O)

<400> SEQUENCE: 58

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Ser
        35                  40

<210> SEQ ID NO 59
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Met(O)

<400> SEQUENCE: 59

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30
```

```
Ser Gly Ala Ser Lys Lys Lys Lys Lys
        35                  40
```

<210> SEQ ID NO 60
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Met(O)

<400> SEQUENCE: 60

```
Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Ser Lys Lys Lys Lys Lys
        35                  40                  45
```

<210> SEQ ID NO 61
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Met(O)

<400> SEQUENCE: 61

```
Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Ser Lys Lys Lys Lys Lys
        35                  40                  45
```

<210> SEQ ID NO 62
<211> LENGTH: 50
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Met(O)
<220> FEATURE:
<221> NAME/KEY: MOD_RES
<222> LOCATION: (34)..(34)
<223> OTHER INFORMATION: Cyclic Imide

<400> SEQUENCE: 62

```
Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Xaa Gly Gly Pro Ser Ser Gly Ala Pro Pro Ser Lys Lys Lys Lys
        35                  40                  45
```

Lys Lys
    50

<210> SEQ ID NO 63
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Met(O)
<220> FEATURE:
<221> NAME/KEY: MOD_RES
<222> LOCATION: (28)..(28)
<223> OTHER INFORMATION: Cyclic Imide

<400> SEQUENCE: 63

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Xaa Gly Gly Pro Ser
            20                  25                  30

Ser Gly Ala Ser
        35

<210> SEQ ID NO 64
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Met(O)
<220> FEATURE:
<221> NAME/KEY: MOD_RES
<222> LOCATION: (34)..(34)
<223> OTHER INFORMATION: Cyclic Imide

<400> SEQUENCE: 64

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Xaa Gly Gly Pro Ser Ser Gly Ala Ser
        35                  40

<210> SEQ ID NO 65
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Met(O)
<220> FEATURE:
<221> NAME/KEY: MOD_RES
<222> LOCATION: (34)..(34)
<223> OTHER INFORMATION: Cyclic Imide

<400> SEQUENCE: 65

```
Asn Glu Glu Glu Glu His Gly Glu Gly Thr Phe Thr Ser Asp Leu
1               5                   10                  15

Ser Lys Gln Met Glu Glu Ala Val Arg Leu Phe Ile Glu Trp Leu
            20                  25                  30

Lys Xaa Gly Gly Pro Ser Ser Gly Ala Ser
        35                  40
```

<210> SEQ ID NO 66
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Met(O)
<220> FEATURE:
<221> NAME/KEY: MOD_RES
<222> LOCATION: (28)..(28)
<223> OTHER INFORMATION: Cyclic Imide

<400> SEQUENCE: 66

```
His Gly Glu Gly Thr Phe Thr Ser Asp Leu Ser Lys Gln Met Glu
1               5                   10                  15

Glu Ala Val Arg Leu Phe Ile Glu Trp Leu Lys Xaa Gly Gly Pro Ser
            20                  25                  30

Ser Gly Ala Ser Lys Lys Lys Lys Lys Lys
        35                  40
```

<210> SEQ ID NO 67
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Met(O)
<220> FEATURE:
<221> NAME/KEY: MOD_RES
<222> LOCATION: (34)..(34)
<223> OTHER INFORMATION: Cyclic Imide

<400> SEQUENCE: 67

```
Lys Lys Lys Lys Lys Lys His Gly Glu Gly Thr Phe Thr Ser Asp Leu
1               5                   10                  15

Ser Lys Gln Met Glu Glu Ala Val Arg Leu Phe Ile Glu Trp Leu
            20                  25                  30

Lys Xaa Gly Gly Pro Ser Ser Gly Ala Ser Lys Lys Lys Lys Lys
        35                  40                  45
```

<210> SEQ ID NO 68
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Met(O)
<220> FEATURE:
<221> NAME/KEY: MOD_RES

```
<222> LOCATION: (34)..(34)
<223> OTHER INFORMATION: Cyclic Imide

<400> SEQUENCE: 68

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Xaa Gly Gly Pro Ser Ser Gly Ala Ser Lys Lys Lys Lys Lys Lys
        35                  40                  45

<210> SEQ ID NO 69
<211> LENGTH: 50
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Met(O)
<220> FEATURE:
<221> NAME/KEY: MOD_RES
<222> LOCATION: (31)..(31)
<223> OTHER INFORMATION: Trp(O2)

<400> SEQUENCE: 69

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Pro Pro Ser Lys Lys Lys Lys
        35                  40                  45

Lys Lys
    50

<210> SEQ ID NO 70
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Met(O)
<220> FEATURE:
<221> NAME/KEY: MOD_RES
<222> LOCATION: (25)..(25)
<223> OTHER INFORMATION: Trp(O2)

<400> SEQUENCE: 70

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Ser
        35

<210> SEQ ID NO 71
<211> LENGTH: 42
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Met(O)
<220> FEATURE:
<221> NAME/KEY: MOD_RES
<222> LOCATION: (31)..(31)
<223> OTHER INFORMATION: Trp(O2)

<400> SEQUENCE: 71

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Ser
        35                  40

<210> SEQ ID NO 72
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Met(O)
<220> FEATURE:
<221> NAME/KEY: MOD_RES
<222> LOCATION: (31)..(31)
<223> OTHER INFORMATION: Trp(O2)

<400> SEQUENCE: 72

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Ser
        35                  40

<210> SEQ ID NO 73
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Met(O)
<220> FEATURE:
<221> NAME/KEY: MOD_RES
<222> LOCATION: (25)..(25)
<223> OTHER INFORMATION: Trp(O2)

<400> SEQUENCE: 73

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Ser Lys Lys Lys Lys Lys Lys
        35                  40
```

```
<210> SEQ ID NO 74
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Met(O)
<220> FEATURE:
<221> NAME/KEY: MOD_RES
<222> LOCATION: (31)..(31)
<223> OTHER INFORMATION: Trp(O2)

<400> SEQUENCE: 74

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Ser Lys Lys Lys Lys Lys Lys
        35                  40                  45

<210> SEQ ID NO 75
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Met(O)
<220> FEATURE:
<221> NAME/KEY: MOD_RES
<222> LOCATION: (31)..(31)
<223> OTHER INFORMATION: Trp(O2)

<400> SEQUENCE: 75

Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asp Gly Gly Pro Ser Ser Gly Ala Ser Lys Lys Lys Lys Lys Lys
        35                  40                  45

<210> SEQ ID NO 76
<211> LENGTH: 50
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Met(O)
<220> FEATURE:
<221> NAME/KEY: MOD_RES
<222> LOCATION: (31)..(31)
<223> OTHER INFORMATION: Trp(O2)
<220> FEATURE:
<221> NAME/KEY: MOD_RES
<222> LOCATION: (34)..(34)
<223> OTHER INFORMATION: Cyclic Imide

<400> SEQUENCE: 76

Lys Lys Lys Lys Lys Lys His Gly Glu Gly Thr Phe Thr Ser Asp Leu
```

```
                 1               5                  10                 15
Ser Lys Gln Met Glu Glu Glu Ala Val Arg Leu Phe Ile Glu Trp Leu
                 20                 25                 30

Lys Xaa Gly Gly Pro Ser Ser Gly Ala Pro Pro Ser Lys Lys Lys Lys
        35                 40                 45

Lys Lys
    50

<210> SEQ ID NO 77
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Met(O)
<220> FEATURE:
<221> NAME/KEY: MOD_RES
<222> LOCATION: (25)..(25)
<223> OTHER INFORMATION: Trp(O2)
<220> FEATURE:
<221> NAME/KEY: MOD_RES
<222> LOCATION: (28)..(28)
<223> OTHER INFORMATION: Cyclic Imide

<400> SEQUENCE: 77

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Xaa Gly Gly Pro Ser
                20                  25                  30

Ser Gly Ala Ser
            35

<210> SEQ ID NO 78
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Met(O)
<220> FEATURE:
<221> NAME/KEY: MOD_RES
<222> LOCATION: (31)..(31)
<223> OTHER INFORMATION: Trp(O2)
<220> FEATURE:
<221> NAME/KEY: MOD_RES
<222> LOCATION: (34)..(34)
<223> OTHER INFORMATION: Cyclic Imide

<400> SEQUENCE: 78

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
                20                  25                  30

Lys Xaa Gly Gly Pro Ser Ser Gly Ala Ser
            35                  40

<210> SEQ ID NO 79
<211> LENGTH: 42
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Met(O)
<220> FEATURE:
<221> NAME/KEY: MOD_RES
<222> LOCATION: (31)..(31)
<223> OTHER INFORMATION: Trp(O2)
<220> FEATURE:
<221> NAME/KEY: MOD_RES
<222> LOCATION: (34)..(34)
<223> OTHER INFORMATION: Cyclic Imide

<400> SEQUENCE: 79

Asn Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Xaa Gly Gly Pro Ser Ser Gly Ala Ser
        35                  40

<210> SEQ ID NO 80
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Met(O)
<220> FEATURE:
<221> NAME/KEY: MOD_RES
<222> LOCATION: (25)..(25)
<223> OTHER INFORMATION: Trp(O2)
<220> FEATURE:
<221> NAME/KEY: MOD_RES
<222> LOCATION: (28)..(28)
<223> OTHER INFORMATION: Cyclic Imide

<400> SEQUENCE: 80

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Xaa Gly Gly Pro Ser
            20                  25                  30

Ser Gly Ala Ser Lys Lys Lys Lys Lys Lys
        35                  40

<210> SEQ ID NO 81
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Met(O)
<220> FEATURE:
<221> NAME/KEY: MOD_RES
<222> LOCATION: (31)..(31)
<223> OTHER INFORMATION: Trp(O2)
<220> FEATURE:
<221> NAME/KEY: MOD_RES
<222> LOCATION: (34)..(34)
```

<223> OTHER INFORMATION: Cyclic Imide

<400> SEQUENCE: 81

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Xaa Gly Gly Pro Ser Ser Gly Ala Ser Lys Lys Lys Lys Lys
        35                  40                  45

<210> SEQ ID NO 82
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Met(O)
<220> FEATURE:
<221> NAME/KEY: MOD_RES
<222> LOCATION: (31)..(31)
<223> OTHER INFORMATION: Trp(O2)
<220> FEATURE:
<221> NAME/KEY: MOD_RES
<222> LOCATION: (34)..(34)
<223> OTHER INFORMATION: Cyclic Imide

<400> SEQUENCE: 82

Asn Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Xaa Gly Gly Pro Ser Ser Gly Ala Ser Lys Lys Lys Lys Lys
        35                  40                  45

<210> SEQ ID NO 83
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Pro Ser
        35

<210> SEQ ID NO 84
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(28)
<223> OTHER INFORMATION: IsoAsp

<400> SEQUENCE: 84

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Pro Ser
        35

<210> SEQ ID NO 85
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(28)
<223> OTHER INFORMATION: Cyclic Imide

<400> SEQUENCE: 85

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Xaa Gly Gly Pro Ser
            20                  25                  30

Ser Gly Ala Pro Pro Pro Ser
        35

<210> SEQ ID NO 86
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Met(O)

<400> SEQUENCE: 86

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 87
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Trp(O2)

<400> SEQUENCE: 87

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

```
Ser Gly Ala Pro Pro Pro Ser
        35

<210> SEQ ID NO 88
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Met(O)

<400> SEQUENCE: 88

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Pro Ser
        35

<210> SEQ ID NO 89
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Met(O)
<220> FEATURE:
<221> NAME/KEY: MOD_RES
<222> LOCATION: (28)..(28)
<223> OTHER INFORMATION: IsoAsp

<400> SEQUENCE: 89

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Pro Ser
        35

<210> SEQ ID NO 90
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Met(O)
<220> FEATURE:
<221> NAME/KEY: MOD_RES
<222> LOCATION: (28)..(28)
<223> OTHER INFORMATION: Cyclic Imide

<400> SEQUENCE: 90

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Xaa Gly Gly Pro Ser
            20                  25                  30
```

```
Ser Gly Ala Pro Pro Pro Ser
        35

<210> SEQ ID NO 91
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Met(O)
<220> FEATURE:
<221> NAME/KEY: MOD_RES
<222> LOCATION: (25)..(25)
<223> OTHER INFORMATION: Trp(O2)

<400> SEQUENCE: 91

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 92
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Trp(O2)

<400> SEQUENCE: 92

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Pro Ser
        35

<210> SEQ ID NO 93
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Trp(O2)
<220> FEATURE:
<221> NAME/KEY: MOD_RES
<222> LOCATION: (28)..(28)
<223> OTHER INFORMATION: IsoAsp

<400> SEQUENCE: 93

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
```

```
                20              25              30

Ser Gly Ala Pro Pro Ser
        35

<210> SEQ ID NO 94
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Trp(O2)
<220> FEATURE:
<221> NAME/KEY: MOD_RES
<222> LOCATION: (28)..(28)
<223> OTHER INFORMATION: Cyclic Imide

<400> SEQUENCE: 94

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Xaa Gly Gly Pro Ser
                20              25                  30

Ser Gly Ala Pro Pro Ser
        35

<210> SEQ ID NO 95
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Met(O)
<220> FEATURE:
<221> NAME/KEY: MOD_RES
<222> LOCATION: (25)..(25)
<223> OTHER INFORMATION: Trp(O2)

<400> SEQUENCE: 95

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
                20              25                  30

Ser Gly Ala Pro Pro Ser
        35

<210> SEQ ID NO 96
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Met(O)
<220> FEATURE:
<221> NAME/KEY: MOD_RES
<222> LOCATION: (25)..(25)
<223> OTHER INFORMATION: Trp(O2)
<220> FEATURE:
<221> NAME/KEY: MOD_RES
```

```
<222> LOCATION: (28)..(28)
<223> OTHER INFORMATION: IsoAsp

<400> SEQUENCE: 96

His Gly Glu Gly Thr Phe Thr Ser Asp Leu Ser Lys Gln Met Glu Glu
1               5                  10                  15

Glu Ala Val Arg Leu Phe Ile Glu Trp Leu Lys Asp Gly Gly Pro Ser
            20                  25                  30

Ser Gly Ala Pro Pro Pro Ser
        35

<210> SEQ ID NO 97
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Met(O)
<220> FEATURE:
<221> NAME/KEY: MOD_RES
<222> LOCATION: (25)..(25)
<223> OTHER INFORMATION: Trp(O2)
<220> FEATURE:
<221> NAME/KEY: MOD_RES
<222> LOCATION: (28)..(28)
<223> OTHER INFORMATION: Cyclic Imide

<400> SEQUENCE: 97

His Gly Glu Gly Thr Phe Thr Ser Asp Leu Ser Lys Gln Met Glu Glu
1               5                  10                  15

Glu Ala Val Arg Leu Phe Ile Glu Trp Leu Lys Xaa Gly Gly Pro Ser
            20                  25                  30

Ser Gly Ala Pro Pro Pro Ser
        35

<210> SEQ ID NO 98
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Trp(O2)

<400> SEQUENCE: 98

His Gly Glu Gly Thr Phe Thr Ser Asp Leu Ser Lys Gln Met Glu Glu
1               5                  10                  15

Glu Ala Val Arg Leu Phe Ile Glu Trp Leu Lys Asp Gly Gly Pro Ser
            20                  25                  30

Ser Gly Ala Pro Pro Ser
        35

<210> SEQ ID NO 99
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (25)..(25)
<223> OTHER INFORMATION: Trp(O2)
<220> FEATURE:
<221> NAME/KEY: MOD_RES
<222> LOCATION: (28)..(28)
<223> OTHER INFORMATION: IsoAsp

<400> SEQUENCE: 99

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Pro Ser
        35

<210> SEQ ID NO 100
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (25)..(25)
<223> OTHER INFORMATION: Trp(O2)
<220> FEATURE:
<221> NAME/KEY: MOD_RES
<222> LOCATION: (28)..(28)
<223> OTHER INFORMATION: Cyclic Imide

<400> SEQUENCE: 100

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Xaa Gly Gly Pro Ser
            20                  25                  30

Ser Gly Ala Pro Pro Ser
        35

<210> SEQ ID NO 101
<211> LENGTH: 7
<212> TYPE: PRT
<213> ORGANISM: Heloderma suspectum

<400> SEQUENCE: 101

Glu Glu Glu Ala Val Arg Leu
1               5

<210> SEQ ID NO 102
<211> LENGTH: 5
<212> TYPE: PRT
<213> ORGANISM: Heloderma suspectum

<400> SEQUENCE: 102

Leu Lys Asn Gly Gly
1               5

<210> SEQ ID NO 103
<211> LENGTH: 4
<212> TYPE: PRT
<213> ORGANISM: Heloderma suspectum

<400> SEQUENCE: 103

Ser Ser Gly Ala
1
```

```
<210> SEQ ID NO 104
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 105
<211> LENGTH: 45
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys Lys Lys Lys Lys Lys
        35                  40                  45

<210> SEQ ID NO 106
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Lys Lys Lys Lys Lys Lys
1               5

<210> SEQ ID NO 107
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (28)..(28)
<223> OTHER INFORMATION: alpha-Asp
<220> FEATURE:
<221> NAME/KEY: MOD_RES
<222> LOCATION: (36)..(38)
<223> OTHER INFORMATION: This region may encompass 0 to 3 Proline
      residues

<400> SEQUENCE: 107

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
```

-continued

```
                      20                  25                  30
Ser Gly Ala Pro Pro Pro Ser
        35

<210> SEQ ID NO 108
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asp Gly Gly Pro Ser
            20                  25                  30

Ser Gly Ala Pro Ser
        35
```

STABILIZED EXENDIN-4 COMPOUNDS

CROSS-REFERENCE TO RELATED APPLICATIONS

This present application claims the benefit of PCT/DK2003/000651 (WO 2004/035623 A2) as filed on 2 Oct. 2003 which International Application claims priority to U.S. Ser. No. 60/415,626 as filed on 2 Oct. 2002. The disclosures of each of said PCT/DK2003/000651 (WO 2004/035623 A2) and U.S. Ser. No. 60/415,626 applications are incorporated herein by reference.

FIELD OF THE INVENTION

The present invention relates to stabilized Exendin-4 compounds and related molecules. In one aspect the invention provides stabilized Exendin-4 agonists that include at least one modified amino acid residue particularly at positions Gln13, Met14, Trp25, or Asn28 of the Exendin-4 (1-39) molecule. Preferred modifications are deaminated, hydrolyzed, oxidized, or isomerized reaction products of the specified amino acid residues corresponding to the same positions in the Exendin-4 (1-39) molecule. Also provided are methods of making and using the stabilized Exendin compounds. The invention has a broad spectrum of uses and provides Exendin-4 compounds having better stability when compared to prior Exendin-4 compositions.

BACKGROUND OF THE INVENTION

A number of hormones that lower blood glucose levels are released from the gastrointestinal mucosa in response to the presence and absorption of nutrients in the gut. These include gastrin, secretin, glucose-dependent insulinotropic polypeptide (GIP) and glucagon-like peptide-1 (GLP-1). The most potent substance known is GLP-1 (Ørskov, 1992, Diabetologia 35:701-711). Glucagon-like peptide 1 (GLP-1) is a product of proglucagon, a 180 amino acid peptide (Drucker, 1998, Diabetes 47:159-169). The overall sequence of proglucagon contains the 29-amino acid sequence of glucagon, the 36 or 37 amino acid sequence of GLP-1 and the 34 amino acid sequence of glucagon-like peptide-2 (GLP-2), an intestinotrophic peptide. GLP-1 has a number of functions. It is a physiological hormone that enhances the effect on insulin secretion in normal humans and is therefore an incretin hormone. In addition, GLP-1 also lowers glucagon concentrations, slows gastric emptying, stimulates (pro)insulin biosynthesis, and enhances insulin sensitivity (Nauck, 1997, Horm. Metab. Res. 47:1253-1258). The peptide also enhances the ability for the β-cells to sense and respond to glucose in subjects with impaired glucose tolerance (Byrne, 1998, Eur. J. Clin. Invest. 28:72-78). The insulinotropic effect of GLP-1 in humans increases the rate of glucose disappearance partly because of increased insulin levels and partly because of enhanced insulin sensitivity (D'Alessio, 1994, Eur. J. Clin. Invest. 28:72-78). This has placed GLP-1 as a promising agent for treatment for type II diabetes. Active fragments of GLP-1 have been found to be GLP-1(7-36) and GLP-1(7-37). However, a major pharmacological problem with native GLP-1 is its short half-life. In humans and rats, GLP-1 is rapidly degraded by dipeptidyl peptidase-IV (DPP-IV) into GLP-1(9-36)amide, acting as an endogenous GLP-1 receptor antagonist. Several strategies circumventing this problem have been proposed, some using inhibitors of DPP-IV and others DPP-IV resistant analogues of GLP-1(7-36)amide.

Exendins, another group of peptides that lower blood glucose levels have some sequence similarity (53%) to GLP-1 [7-36]$NH_2$ (Goke et al., 1993, J. Biol. Chem. 268:19650-55). The Exendins are found in the venom of Helodermatidae or beaded lizards. Exendin-3 is present in the venom of *Heloderma horridum*, the Mexican beaded lizard and Exendin-4 is present in the venom of *Heloderma suspectum*, the Gila monster. Exendin-4 differs from Exendin-3 at just positions two and three. The cDNA encoding the Exendin-4 precursor protein, a 47 amino acid peptide fused to the amino terminus of Exendin-4 has been cloned and sequenced (Pohl et al., 1998, J. Biol. Chem. 273:9778-9784 and WO98/35033).

Exendin-4 is a strong GLP-1 receptor agonist on isolated rat insulinoma cells (Goke et al., 1993, J. Biol. Chem. 268: 19650-55). Exendin-4 given systemically lowers blood glucose levels by 40% in diabetic db/db mice (WO99/07404). Recently, Grieg et al. (1999, Diabetologia 42:45-50) have shown a long lasting blood glucose lowering effect of once daily intraperitoneal injection of Exendin-4 to diabetic ob/ob mice. U.S. Pat. No. 5,424,286 discloses that a considerable portion of the N-terminal sequence is essential in order to preserve insulinotropic activity (Exendin-4 (1-31) and $Y^{31}$-Exendin-4 (1-31)) whereas an N-terminally truncated Exendin (Exendin-4 (9-39) has inhibitory properties.

The use of Exendin-3, Exendin-4 and Exendin agonists has been proposed for the treatment of diabetes mellitus, reducing gastric motility and delaying gastric emptying and the prevention of hyperglycemia (U.S. Pat. No. 5,424,286, WO98/05351) as well as for the reduction of food intake (WO98/30231). Ways of obtaining novel compounds by modifying the native Exendin sequences have been proposed. One way is to attach lipophilic substituents to the molecule, e.g. as described in WO 99/43708 which discloses derivatives of Exendin with just one lipophilic substituent attached to the C-terminal amino acid residue.

A major approach has been to devise Exendin analogues characterised by amino acid substitutions and/or C-terminal truncation of the native Exendin-4 sequence. This approach is represented by the compounds of WO99/07404, WO 99/25727 and WO 99/25728.

WO99/07404 discloses Exendin agonists having a general formula I that defines a peptide sequence of 39 amino acid residues with Gly Thr in positions 4-5, Ser Lys Gln in positions 11-13, Glu Glu Glu Ala Val Arg Leu (SEQ ID NO: 101) in positions 15-21, Leu Lys Asn Gly Gly (SEQ ID NO: 102) in positions 26-30, Ser Ser Gly Ala (SEQ ID NO: 103) in positions 32-35, and wherein the remaining positions may be occupied by wild-type Exendin amino acid residues or may be occupied by specified amino acid substitutions. The formula I does not cover any Exendin agonists or analogues having specific amino acid deletions and/or being conjugates as described herein, such as the novel compounds desPro$^{36}$-Exendin-4 (1-39) (SEQ ID NO: 104), Exendin-4 (1-39)-$K_6$ (SEQ ID NO: 105) or desPro$^{36}$-Exendin-4 (1-39)-$K_6$ (SEQ ID NO: 1).

WO 99/25727 discloses Exendin agonists having a general formula I that defines a peptide sequence of from 28 to 38 amino acid residues with Gly in position 4 and Ala in position 18, and wherein the remaining positions may be occupied by wild-type Exendin amino acid residues or may be occupied by specified amino acid substitutions. Formula I does not comprise a peptide sequence having Ser as the C-terminal amino acid and Exendin agonists or analogues having specific amino acid deletions and/or being conjugates as described herein, such as the novel compounds desPro$^{36}$-Exendin-4 (1-39) (SEQ ID NO: 104), Exendin-4 (1-39)-$K_6$ (SEQ ID NO: 105) or desPro$^{36}$-Exendin-4 (1-39)-$K_6$ (SEQ ID NO: 1). Further, formula II of WO 99/25727 defines a peptide sequence similar to formula I, but including Exendin derivatives having a C(1-10)alkanoyl or cycloalkylalkanoyl substituent on lysine in position 27 or 28.

When treating inappropriate post-prandial blood glucose levels the compounds are administered frequently, for example one, two or three times a day.

WO 99/25728 discloses Exendin agonists having a general formula I that defines a peptide sequence of from 28 to 39 amino acid residues with fixed Ala in position 18, and wherein the remaining positions may be occupied by wild-type Exendin amino acid residues or may be occupied by specified amino acid substitutions. Said Exendin agonists all correspond to a truncated Exendin analogue having a varying degree of amino acid substitutions. Peptide sequences of from 34 to 38 amino acid residues do not have Ser C-terminally. A peptide sequence of 39 amino acid residues may have either Ser or Tyr C-terminally, but no further residues. Exendin agonists or analogues having specific amino acid deletions and/or being conjugates according to the invention described herein are not comprised by formula I. Further, formula II defines a peptide sequence similar to formula I, but including Exendin derivatives having a C(1-10)alkanoyl or cycloalkylalkanoyl substituent on lysine in position 27 or 28.

WO 99/46283 (published Sep. 16, 1999) discloses peptide conjugates comprising a pharmacologically active peptide X and a stabilising peptide sequence Z of 4-20 amino acid residues covalently bound to X, where said conjugates are characterised in having an increased half-life compared to the half-life of X. X may be Exendin-4 or Exendin-3.

It would be desirable to have Exendin compositions that can provide better stability than prior compounds. Further desirable would be to have Exendin compositions that can resist degradation. Such compositions would be especially useful in settings where significant storage times are expected and/or where there is risk from unwanted oxidation, hydrolysis or deamination reactions.

SUMMARY OF THE INVENTION

The present invention generally relates to stabilized Exendin-4 compounds and related compositions. In one aspect, the invention provides stabilized Exendin compounds, particularly Exendin-4 agonists, that include at least one modified amino acid residue at positions Gln13, Met14, Trp25, or Asn28 of the Exendin-4 (1-39) molecule. Also provided are methods of making and using the stabilized Exendin-4 compositions. The invention has a broad spectrum of uses including providing Exendin-4 compositions with better stability and storage properties when compared with prior Exendin-4 compositions and related compounds.

We have discovered that it is possible to stabilize Exendin-4 compounds and related compositions by modifying particular Exendin amino acids therein. Preferred modifications according to the invention are deaminated, hydrolyzed, oxidized, or isomerized reaction products of the specified amino acid residues of the Exendin-4 (1-39) molecule. Such compounds can be readily made by one or a combination of standard techniques including exposing Exendin-4 (1-39) to pharmaceutically acceptable formulation procedures, exposing the molecule to potentially reactive conditions such as contact with water, oxygen, light, heat or the like, or otherwise providing conditions conducive to spontaneous or semi-spontaneous degradation of amino acids corresponding to at least one of Gln13, Met14, Trp25, or Asn28 of the Exendin-4 (1-39) molecule.

Practice of preferred embodiments of the invention provide substantial advantages. For instance, use of the invention is able to provide stabilized Exendin-4 compounds that feature more reliable activity particularly over prolonged storage times. Such stabilized Exendin-4 molecules and related compositions can assist medical uses including clinical studies and other uses by providing more reproducible and consistent agonist activity. This feature of the invention is particularly important when multiple Exendin-4 preparations (lots) are needed. That is, by stabilizing the Exendin-4 compounds and related molecules according to the invention, it is now possible to improve consistency between lots.

Additionally, use of the invention can now provide more consistent dosing of Exendin-4 compositions and related molecules. That is, the stabilized compounds of the invention are less apt to degrade and thus can provide more reliable therapeutic activity. This feature of the invention is particularly important when it is desirable to produce Exendin-4 and related molecules having relatively consistent activity or good stability on a moderate or large scale.

By the phrase "Exendin-4 compound or related molecule" including plural forms is meant Exendin-4 (1-39), or a variant, analogue or derivative thereof as defined in this application. Illustrative is Exendin-4 (1-39) and derivatives thereof that include a deletion of between from about 1 to about 5 amino acids that corresponds to positions 34, 35, 36, 37 or 38 of Exendin-4. Optionally, such derivatives further include at least one peptide Z as defined herein. Such compounds or molecules are "stabilized" according to the invention (eg., a stabilized Exendin-4 (1-39) compound) by modifying at least one of the amino acid residues: Gln13, Met14, Trp25, or Asn28 of the Exendin-4 (1-39) molecule. Preferably, one or two of such amino acids are modified as discussed although more can be to suit an intended use.

Accordingly, and in one embodiment, the invention provides a compound that includes at least one stabilized Exendin-4 (1-39), preferably one, two or three of same, preferably one of such a stabilized Exendin-4 (1-39). In one embodiment, the compound includes:

a) a deletion of 0 to 5 amino acids at positions corresponding to positions 34-38 of Exendin-4 (1-39), b) optionally, at least one peptide sequence Z comprising 4-20 amino acid units covalently bound to said compound; and at least one of the following:

i) an Asn residue having a deaminated side chain, an Asn residue having hydrolyzed side chain or a structural isomer of an Asp residue, wherein the Asn or Asp residue corresponds to position 28 of Exendin-4, ii) an oxidized methionine residue corresponding to position 14 of Exendin-4, iii) an oxidized tryptophan residue corresponding to position 25 of Exendin-4, iv) a deaminated or hydrolyzed Gln corresponding to position 13 of Exendin-4 and a pharmaceutically acceptable salt or solvate thereof.

In one embodiment of the forgoing compound, the stabilized Exendin-4 (1-39) includes at least one L-amino acid residue or at least one D-amino acid residue. Alternatively, the compound includes combinations of L- and D-amino acid residues.

In another aspect, the present invention provides a compound that includes at least one stabilized Exendin-4 (1-39), preferably two, three or four of same, more preferably one of such stabilized Exendin-4 (1-39) molecules. In one embodiment, the compound includes at least one of:

i) an Asn residue having a deaminated side chain, an Asn residue having hydrolyzed side chain or a structural isomer of an Asp residue, wherein the Asn or Asp residue corresponds to position 28 of Exendin-4,
ii) an oxidized methionine residue corresponding to position 14 of Exendin-4,
iii) an oxidized tryptophan residue corresponding to position 25 of Exendin-4,
iv) a deaminated or hydrolyzed Gln corresponding to position 13 of Exendin-4;

and a pharmaceutically acceptable salt or solvate thereof.

Further provided are pharmaceutically acceptable compositions that include at least one, preferably two, three or four of the stabilized Exendin-4 (1-39) molecules, more preferably one of such compounds. Examples of such compositions are provided below.

In another aspect, the invention provides a method of making a stabilized Exendin-4 composition or related molecule as disclosed herein. In one embodiment, the method includes at least one of the following steps:
a) obtaining Exendin-4 (1-39) or a variant, analogue, or derivative thereof; and
b) incubating the Exendin-4 (1-39) or the variant, analogue, or derivative thereof under conditions sufficient to introduce at least one of the following amino acids therein:
i) an Asn residue having a deaminated side chain, an Asn residue having hydrolyzed side chain or a structural isomer of an Asp residue, wherein the Asn or Asp residue corresponds to position 28 of Exendin-4,
ii) an oxidized methionine residue corresponding to position 14 of Exendin-4,
iii) an oxidized tryptophan residue corresponding to position 25 of Exendin-4
iv) a deaminated or hydrolyzed Gln corresponding to position 13 of Exendin-4;

and a pharmaceutically acceptable salt or solvate thereof.

It will often be preferred to make the stabilized Exendin-4 molecules of the invention synthetically or semi-synthetically. An example of such a method is described below and includes use of the Merrifield peptide synthesis technique.

In particular embodiments the foregoing methods further include the step of detecting presence or absence of at least one of amino acids (i)-(iv). Alternatively, or in addition, the method can include identifying at least one of the amino acids (i)-(iv) in the composition. Methods for detecting and identifying the modified amino acids are discussed below.

In another embodiment, the invention features a method of making the stabilized Exendin-4 compound and related molecules disclosed herein. Typical of such methods includes at least one of the following steps:
a) obtaining Exendin-4 (1-39) or a variant, analogue or derivative thereof,
b) contacting the Exendin-4 (1-39) or the variant, analogue or derivative with at least one pharmaceutically acceptable carrier or vehicle to produce a mixture; and
c) incubating the mixture under conditions sufficient to introduce at least one of the following amino acids therein:
i) an Asn residue having a deaminated side chain, an Asn residue having hydrolyzed side chain or a structural isomer of an Asp residue, wherein the Asn or Asp residue corresponds to position 28 of Exendin-4,
ii) an oxidized methionine residue corresponding to position 14 of Exendin-4,
iii) an oxidized tryptophan residue corresponding to position 25 of Exendin-4
iv) a deaminated or hydrolyzed Gln corresponding to position 13 of Exendin-4;

and a pharmaceutically acceptable salt or solvate thereof.

Such a method can also further include the step of detecting presence or absence of at least one of the amino acid residues (i)-(iv). Alternatively, or in addition, the method can include identifying at least one of the amino acids (i)-(iv) in the composition.

In another aspect, the invention provides a method of stabilizing Exendin-4 (1-39) or a variant, analogue or derivative thereof. In one embodiment, the method includes at least one of the following steps:
a) obtaining Exendin-4 (1-39) or a variant, derivative or analogue thereof; and
b) incubating the Exendin-4 (1-39) or the variant, derivative or analogue under conditions sufficient to introduce at least one of the following amino acid residues therein:
i) an Asn residue having a deaminated side chain, an Asn residue having hydrolyzed side chain or a structural isomer of an Asp residue, wherein the Asn or Asp residue corresponds to position 28 of Exendin-4,
ii) an oxidized methionine residue corresponding to position 14 of Exendin-4,
iii) an oxidized tryptophan residue corresponding to position 25 of Exendin-4; and
iv) a deaminated or hydrolyzed Gln corresponding to position 13 of Exendin-4;

and a pharmaceutically acceptable salt or solvate thereof.

In another aspect, the invention provides a method for treating diabetes type 1 or type 2, insulin resistance syndrome, impaired glucose tolerance (IGT), obesity, eating disorders, hyperglycemia, metabolic disorders, and gastric disease. In one embodiment, the method includes administering a therapeutically effective amount of at least one of the stabilized Exendin-4 compounds or related molecules disclosed herein.

The invention also provides a method for treating disease states associated with elevated blood glucose levels. In one embodiment, the method includes administering a therapeutically effective amount of at least one of the stabilized Exendin-4 compounds or related molecules disclosed herein.

Also provided is a method for regulation of blood glucose levels. In one embodiment, the method includes administering a therapeutically effective amount of at least one of at least one of the stabilized Exendin-4 compounds or related molecules disclosed herein.

The invention also provides a method for regulation of gastric emptying. In one embodiment, the method includes administering a therapeutically effective amount of at least one of the stabilized Exendin-4 compounds or related molecules provided herein.

The present invention also provides a method of stimulating insulin release in a mammal. In one embodiment, the method includes administering an effective insulinotropic amount of at least one of the stabilized Exendin-4 compounds disclosed herein.

Additionally provided is a method of lowering blood glucose level in a mammal. In one embodiment, the method includes administering an amount of at least one of the stabilized Exendin-4 compounds or related molecules described herein in an amount effective to lower blood glucose level in said mammal.

The invention also provides a method of lowering plasma lipid level in a mammal. In one example, the method includes administering an amount of at least one of the stabilized Exendin-4 compounds described herein in an amount effective to lower plasma lipid level in said mammal.

Also provided is a method of reducing mortality and morbidity after myocardial infarction in a mammal. In one embodiment, the method includes administering an amount of at least one of the stabilized Exendin-4 compounds disclosed herein in an amount effective to reduce mortality and morbidity after myocardial infarction.

Also provided is a method of stimulating insulin release in a mammal. In one embodiment, the method includes administering an effective insulinotropic amount of at least one of the stabilized Exendin-4 compounds provided herein.

Preferably, the mammal featured in each of the foregoing methods is a primate, preferably a human patient in need of treatment.

FIGURES

Figure 1:
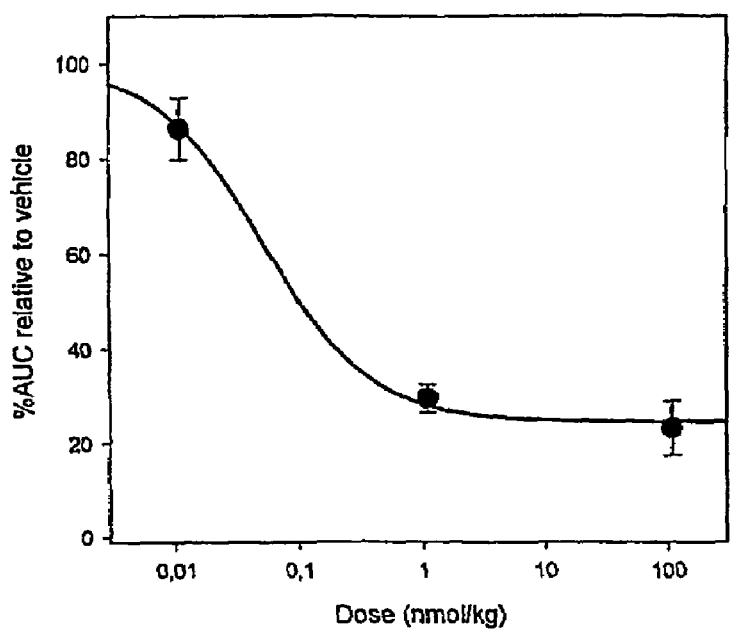
FIG. 1 shows the effect of Compound 1 on glucose tolerance in mice.

FIG. 9 shows the sequences of Compound 1 (des $Pro^{36}$ Exendin-4 (1-39)-$K_6$) and stabilized compounds of Compound 1 (SEQ ID NO: 1), namely Compound 2 (SEQ ID NO: 2), 3 (SEQ ID NO: 3), 4 (SEQ ID NO: 4), 5 (SEQ ID NO: 5), 6 (SEQ ID NO: 6), 7 (SEQ ID NO: 7), 11 (SEQ ID NO: 11), 12 (SEQ ID NO: 12), 13 (SEQ ID NO: 13), and 14 (SEQ ID NO: 14) as well as stabilized compounds of Exendin-4 (1-39), namely Compounds 8 (SEQ ID NO: 8), 9 (SEQ ID NO: 9), and 10 (SEQ ID NO: 10).

DETAILED DESCRIPTION OF THE INVENTION

As discussed, the invention provides stabilized Exendin agonists that include at least one modified amino acid residue particularly at positions Gln13, Met14, Trp25, or Asn28 of the Exendin-4 (1-39) molecule. Preferred modifications are deaminated, hydrolyzed, oxidized, or isomerized reaction products of the specified amino acid residues of the Exendin-4 (1-39) molecule. Also provided are methods of making and using the stabilized Exendin compounds.

Preferred stabilized Exendin-4 (1-39) compounds and pharmaceutically acceptable salt thereof which include:
a) a deletion of 0 to 5 amino acids at positions corresponding to positions 34-38 of Exendin-4,
b) optionally, at least one peptide sequence Z comprising 4-20 amino acid units covalently bound to said variant; and at least one of the following:
  i) an Asn residue having a deaminated side chain, an Asn residue having hydrolyzed side chain or a structural isomer of an Asp residue, wherein the Asn or Asp residue corresponds to position 28 of Exendin-4,
  ii) an oxidized methionine residue corresponding to position 14 of Exendin-4,
  iii) an oxidized tryptophan residue corresponding to position 25 of Exendin,
  iv) a deaminated or hydrolyzed Gln corresponding to position 13 of Exendin-4;

and a pharmaceutically acceptable salt or solvate thereof.

In one embodiment, the Asn residue is an α-aspartate (Asp) or β-aspartate (isoaspartyl) residue or the Asn residue is an Cyclic imide. In another embodiment the oxidized methionine residue is a methioninyl sulfoxide or a methioninyl sulfone. In embodiments in which the Cyclic imide is derived from an Asp or Gln residue, the cyclyzed product is sometimes referred to herein as an aspartimide or glutimide, respectively.

Alternatively, or in addition, the oxidized tryptophan residue includes an oxidized 3H indol-3-yl group. Other examples include an oxidized tryptophan residue that is N-formylkynurenine (NFK), 3-hydroxykynurenine (3-OH-KYN), hydroxytryptophan (HTRP), or kynurenine (KYN).

In embodiments in which the stabilized Exendin-4 compound or related composition includes at least one Z peptide and preferably one or two of same, Z comprises at least one Lys amino acid unit, typically between about 4 to about 20 Lys amino acid units, preferably about 6 Lys amino acid units.

In embodiments in which the stabilized Exendin-4 compound or related composition includes at least one Z peptide and preferably one or two of same, Z comprises at least one Lys amino acid unit, typically between about 4 to about 20 Lys amino acid units, preferably about 6 Lys (SEQ ID NO: 106) amino acid units.

More particular stabilized Exendin-4 (1-39) compounds according to the invention are represented by the following sequences:

des $Pro^{36}$ [$Asp^{28}$]Exendin-4 (1-39) (SEQ ID NO: 15),
des $Pro^{36}$ [$IsoAsp^{28}$]Exendin-4 (1-39) (SEQ ID NO: 16),
des $Pro^{36}$ [Cyclic imide$^{28}$]Exendin-4 (1-39) (SEQ ID NO: 17),
des $Pro^{36}$ [$Met(O)^{14}$]Exendin-4 (1-39) (SEQ ID NO: 18),
des $Pro^{36}$ [$Trp(O_2)^{25}$]Exendin-4 (1-39) (SEQ ID NO: 19),
des $Pro^{36}$ [$Met(O)^{14}$, $Asp^{28}$]Exendin-4 (1-39) (SEQ ID NO: 20),
des $Pro^{36}$ [$Met(O)^{14}$, $IspAsp^{28}$]Exendin-4 (1-39) (SEQ ID NO: 21),
des $Pro^{36}$ [$Met(O)^{14}$, Cyclic imide$^{28}$]Exendin-4 (1-39) (SEQ ID NO: 22),
des $Pro^{36}$ [$Met(O)^{14}$, $Trp(O_2)^{25}$]Exendin-4 (1-39) (SEQ ID NO: 23),
des $Pro^{36}$ [$Met(O)^{14}$, $Trp(O_2)^{25}$, $Asp^{28}$]Exendin-4 (1-39) (SEQ ID NO: 24),
des $Pro^{36}$ [$Met(O)^{14}$, $Trp(O_2)^{25}$, $IsoAsp^{28}$]Exendin-4 (1-39) (SEQ ID NO: 25),
des $Pro^{36}$ [$Met(O)^{14}$, $Trp(O_2)^{25}$, Cyclic imide$^{28}$]Exendin-4 (1-39) (SEQ ID NO: 26), or a pharmaceutically acceptable salter solvate thereof.

With respect to any of the forgoing stabilized Exendin-4 (1-39) compounds, the compounds may further include a deaminated or hydrolyzed Gln corresponding to position 13 of Exendin-4.

In one embodiment of the forgoing compounds, each sequence is attached at the N- or C-terminus to the following group: -$Lys_6$-$NH_2$ (SEQ ID NO: 106). Preferably, the group is attached to the C-terminus of the sequence.

Additionally specific stabilized Exendin-4 (1-39) compounds include the following sequences:

H-(Lys)$_6$-des $Pro^{36}$[$Asp^{28}$]Exendin-4 (1-39)-$Lys_6$-$NH_2$ (SEQ ID NO: 27),
des $Asp^{28}Pro^{36}$, $Pro^{37}$, $Pro^{38}$Exendin-4 (1-39)-$NH_2$ (SEQ ID NO: 28),
H-(Lys)$_6$-des $Pro^{36}$, $Pro^{37}$, $Pro^{38}$[$Asp^{28}$]Exendin-4 (1-39)-$NH_2$ (SEQ ID NO: 29),
H-Asn-(Glu)$_5$des $Pro^{36}$, $Pro^{37}$, $Pro^{38}$[$Asp^{28}$]Exendin-4 (1-39)-$NH_2$ (SEQ ID NO: 30), des Pro$^{38}$, Pro$^{37}$, Pro$^{38}$[Asp$^{28}$]Exendin-4 (1-39)-(Lys)$_6$-NH$_2$ (SEQ ID NO: 31), H-(Lys)$_6$-des Pro$^{36}$, Pro$^{37}$, Pro$^{38}$[Asp$^{28}$]Exendin-4 (1-39)-(Lys)$_6$-NH$_2$ (SEQ ID NO: 32), H-Asn-(Glu)$_5$-des Pro$^{36}$, Pro$^{37}$, Pro$^{38}$[Asp$^{28}$]Exendin-4 (1-39)-(Lys)$_6$-NH$_2$ (SEQ ID NO: 33), H-(Lys)$_6$-des Pro$^{36}$[Cyclic imide]Exendin-4 (1-39)-Lys$_6$-NH$_2$ (SEQ ID NO: 34), des Pro$^{36}$, Pro$^{37}$, Pro$^{38}$[Cyclic imide$^{28}$]Exendin-4 (1-39)-NH$_2$ (SEQ ID NO: 35), H-(Lys)$_6$-des Pro$^{36}$, Pro$^{37}$, Pro$^{38}$[Cyclic imide$^{28}$]Exendin-4 (1-39)-NH$_2$ (SEQ ID NO: 36), H-Asn-(Glu)$_5$-des Pro$^{36}$, Pro$^{37}$, Pro$^{38}$[Cyclic imide$^{28}$]Exendin-4 (1-39)-NH$^2$ (SEQ ID NO: 37), des Pro$^{36}$, Pro$^{37}$, Pro$^{38}$[Cyclic imide$^{28}$]Exendin-4 (1-39)-(Lys)$_6$-NH$_2$ (SEQ ID NO: 38), H-(Lys)$_6$ des Pro$^{36}$, Pro$^{37}$, Pro$^{38}$[Cyclic imide$^{28}$]Exendin-4 (1-39)-(Lys)$_6$-NH$_2$ (SEQ ID NO: 39), H-Asn-(Glu)$_5$-des Pro$^{36}$, Pro$^{37}$, Pro$^{38}$[Cyclic imide$^{28}$]Exendin-4 (1-39)-(Lys)$_8$-NH$_2$ (SEQ ID NO: 40), H-(Lys)$_6$-des Pro$^{36}$[Trp(O$_2$)$^{25}$, Asp$^{28}$]Exendin-4 (1-39)-Lys$_6$-NH$_2$ (SEQ ID NO: 41), H-des Asp$^{28}$Pro$^{36}$, Pro$^{37}$, Pro$^{38}$[Trp(O$_2$)$^{25}$]Exendin-4 (1-39)-NH$_2$ (SEQ ID NO: 42), H-(Lys)$_6$-des Pro$^{36}$, Pro$^{37}$, Pro$^{38}$[Trp(O$_2$)$^{25}$, Asp$^{28}$]Exendin-4 (1-39)-NH$_2$ (SEQ ID NO: 43), H-Asn-(Glu)$_5$-des Pro$^{36}$, Pro$^{37}$, Pro$^{38}$[Trp(O$_2$)$^{25}$, Asp$^{28}$]Exendin-4 (1-39)-NH$_2$ (SEQ ID NO: 44), des Pro$^{36}$, Pro$^{37}$, Pro$^{38}$[Trp(O$_2$)$^{25}$, Asp$^{28}$]Exendin-4 (1-39)-(Lys)$_6$-NH$_2$ (SEQ ID NO: 45), H-(Lys)$_6$-des Pro$^{36}$, Pro$^{37}$, Pro$^{38}$[Trp(O$_2$)$^{25}$, Asp$^{28}$]Exendin-4 (1-39)-(Lys)$_6$-NH$_2$ (SEQ ID NO: 46), H-Asn-(Glu)$_5$-des Pro$^{36}$, Pro$^{37}$, Pro$^{38}$[Trp(O$_2$)$^{25}$, Asp$^{26}$]Exendin-4 (1-39)-(Lys)$_6$-NH$_2$ (SEQ ID NO: 47), H-(Lys)$_6$-des Pro$^{36}$[Trp(O$_2$)$^{25}$, Cyclic imide$^{28}$]Exendin-4 (1-39)-Lys$_6$-NH$_2$ (SEQ ID NO: 48), des Cyclic imide$^{28}$Pro$^{36}$, Pro$^{37}$, Pro$^{38}$[Trp(O$_2$)$^{26}$]Exendin-4 (1-39)-NH$_2$ (SEQ ID NO: 49), H-(Lys)$_6$-des Pro$^{36}$, Pro$^{37}$, Pro$^{38}$[Trp(O$_2$)$^{25}$, Cyclic imide$^{28}$]Exendin-4 (1-39)-NH$_2$ (SEQ ID NO: 50), H-Asn-(Glu)$_5$-des Pro$^{36}$, Pro$^{37}$, Pro$^{38}$[Trp(O$_2$)$^{25}$, Cyclic imide$^{28}$]Exendin-4 (1-39)-NH$_2$ (SEQ ID NO: 51), des Pro$^{36}$, Pro$^{37}$, Pro$^{38}$[Trp(O$_2$)$^{25}$, Cyclic imide$^{28}$]Exendin-4 (1-39)-(Lys)$_6$-NH$_2$ (SEQ ID NO: 52), H-(Lys)$_6$-des Pro$^{36}$, Pro$^{37}$, Pro$^{38}$[Trp(O$_2$)$^{25}$, Cyclic imide$^{28}$]Exendin-4 (1-39)-(Lys)$_6$-NH$_2$ (SEQ ID NO: 53), H-Asn-(Glu)$_5$-des Pro$^{36}$, Pro$^{37}$, Pro$^{38}$[Trp(O$_2$)$^{25}$, Cyclic imide$^{28}$]Exendin-4 (1-39)-(Lys)$_6$-NH$_2$ (SEQ ID NO: 54), H-(Lys)$_6$-des Pro$^{36}$[Met(O)$^{14}$, Asp$^{28}$]Exendin-4 (1-39)-Lys$_6$-NH$_2$ (SEQ ID NO: 55), des Met(O)$^{14}$Asp$^{28}$Pro$^{36}$, Pro$^{37}$, Pro$^{38}$Exendin-4 (1-39)-NH$_2$ (SEQ ID NO: 56), H-(Lys)$_6$-des Pro$^{36}$, Pro$^{37}$, Pro$^{38}$[Met(O)$^{14}$, Asp$^{28}$]Exendin-4 (1-39)-NH$_2$ (SEQ ID NO: 57), H-Asn-(Glu)$_5$-des Pro$^{36}$, Pro$^{37}$, Pro$^{38}$[Met(O)$^{14}$, Asp$^{28}$]Exendin-4 (1-39)-NH$_2$ (SEQ ID NO: 58), des Pro$^{38}$, Pro$^{37}$, Pro$^{38}$[Met(O)$^{14}$, Asp$^{28}$]Exendin-4 (1-39)-(Lys)$_6$-NH$_2$ (SEQ ID NO: 59), H-(Lys)$_6$-des Pro$^{36}$, Pro$^{37}$, Pro$^{38}$[Met(O)$^{14}$, Asp$^{28}$]Exendin-4 (1-39)-(Lys)$_6$-NH$_2$ (SEQ ID NO: 60), H-Asn-(Glu)$_5$des Pro$^{36}$, Pro$^{37}$, Pro$^{38}$[Met(O)$^{14}$, Asp$^{28}$]Exendin-4 (1-39)-(Lys)$_8$—NH$_2$ (SEQ ID NO: 61), H-Lys$_6$-des Pro$^{36}$[Met(O)$^{14}$, Cyclic imide$^{28}$]Exendin-4 (1-39)-Lys$_6$-NH$_2$ (SEQ ID NO: 62), des Pro$^{36}$, Pro$^{37}$, Pro$^{38}$[Met(O)$^{14}$, Cyclic imide$^{28}$]Exendin-4 (1-39)-NH$_2$ (SEQ ID NO: 63), H-(Lys)$_6$-des Pro$^{36}$, Pro$^{37}$, Pro$^{38}$[Met(O)$^{14}$, Cyclic imide$^{28}$]Exendin-4 (1-39)-NH$_2$ (SEQ ID NO: 64), H-Asn-(Glu)$_5$-des Pro$^{36}$, Pro$^{37}$, Pro$^{38}$[Met(O)$^{14}$, Cyclic imide$^{28}$]Exendin-4 (1-39)-NH$_2$ (SEQ ID NO: 65), des Pro$^{36}$, Pro$^{37}$, Pro$^{38}$[Met(O)$^{14}$, Cyclic imide$^{28}$]Exendin-4 (1-39)-(Lys)$_6$-NH$_2$ (SEQ ID NO: 66), H-(Lys)$_6$-des Pro$^{36}$, Pro$^{37}$, Pro$^{38}$[Met(O)$^{14}$, Cyclic imide$^{28}$]Exendin-4 (1-39)-(Lys)$_6$-NH$_2$ (SEQ ID NO: 67), H-Asn-(Glu)$_5$-des Pro$^{36}$, Pro$^{37}$, Pro$^{38}$[Met(O)$^{14}$, Cyclic imide$^{28}$]Exendin-4 (1-39)-(Lys)$_6$-NH$_2$ (SEQ ID NO: 68), H-Lys$_6$-des Pro$^{36}$[Met(O)$^{14}$, Trp(O$_2$)$^{25}$, Asp$^{28}$]Exendin-4 (1-39)-Lys$_6$-NH$_2$ (SEQ ID NO: 69), H-des Asp$^{28}$Pro$^{36}$, Pro$^{37}$, Pro$^{38}$[Met(O)$^{14}$, Trp(O$_2$)$^{25}$]Exendin-4 (1-39)-NH$_2$ (SEQ ID NO: 70), H-(Lys)$_6$-des Pro$^{36}$, Pro$^{37}$, Pro$^{38}$[Met(O)$^{14}$, Trp(O$_2$)$^{25}$, Asp$^{28}$]Exendin-4 (1-39)-NH$_2$ (SEQ ID NO: 71), H-Asn-(Glu)$_5$-des Pro$^{36}$, Pro$^{37}$, Pro$^{38}$[Met(O)$^{14}$, Trp(O$_2$)$^{25}$, Asp$^{28}$]Exendin-4 (1-39)-NH$_2$ (SEQ ID NO: 72), des Pro$^{36}$, Pro$^{37}$, Pro$^{38}$[Met(O)$^{14}$, Trp(O$_2$)$^{25}$, Asp$^{28}$]Exendin-4 (1-39)-(Lys)$_6$-NH$_2$ (SEQ ID NO: 73), H-(Lys)$_6$-des Pro$^{36}$, Pro$^{37}$, Pro$^{38}$[Met(O)$^{14}$, Trp(O$_2$)$^{25}$, Asp$^{28}$]Exendin-4 (1-39)-(Lys)$_6$-NH$_2$ (SEQ ID NO: 74), H-Asn-(Glu)$_5$-des Pro$^{36}$, Pro$^{37}$, Pro$^{38}$[Met(O)$^{14}$, Trp(O$_2$)$^{25}$, Asp$^{28}$]Exendin-4 (1-39)-(Lys)$_6$-NH$_2$ (SEQ ID NO: 75), H-Lys$_6$-des Pro$^{36}$[Met(O)$^{14}$, Trp(O$_2$)$^{25}$, Cyclic imide$^{28}$]Exendin-4 (1-39)-Lys$_6$-NH$_2$ (SEQ ID NO: 76), des Cyclic imide$^{26}$Pro$^{36}$, Pro$^{37}$, Pro$^{38}$[Met(O)$^{14}$, Trp(O$_2$)$^{25}$]Exendin-4 (1-39)-NH$_2$ (SEQ ID NO: 77), H-(Lys)$_6$-des Pro$^{36}$, Pro$^{37}$, Pro$^{38}$[Met(O)$^{14}$, Trp(O$_2$)$^{25}$, Cyclic imide$^{28}$]Exendin-4 (1-39)-NH$_2$ (SEQ ID NO: 78), H-Asn-(Glu)$_5$-des Pro$^{36}$, Pro$^{37}$, Pro$^{38}$[Met(O)$^{14}$, Trp(O$_2$)$^{25}$, Cyclic imide$^{28}$]Exendin-4 (1-39)-NH$_2$ (SEQ ID NO: 79), des Pro$^{36}$, Pro$^{37}$, Pro$^{38}$[Met(O)$^{14}$, Trp(O$_2$)$^{25}$, Cyclic imide$^{28}$]Exendin-4 (1-39)(Lys)$_6$-NH$_2$ (SEQ ID NO: 80), H-(Lys)$_6$-des Pro$^{36}$, Pro$^{37}$, Pro$^{38}$[Met(O)$^{14}$, Trp(O$_2$)$^{25}$, Cyclic imide$^{28}$]Exendin-4 (1-39)-(Lys)$_6$-NH$_2$ (SEQ ID NO: 81), H-Asn-(Glu)$_5$-des Pro$^{36}$, Pro$^{37}$, Pro$^{38}$[Met(O)$^{14}$, Trp(O$_2$)$^{25}$, Cyclic imide$^{28}$]Exendin-4 (1-39)-(Lys)$_6$-NH$_2$ (SEQ ID NO: 82), or a pharmaceutically acceptable salt or solvate thereof.

With respect to any of the foregoing stabilized Exendin-4 (1-39) compounds, the compounds may further include a deaminated or hydrolyzed Gln corresponding to position 13 of Exendin-4.

As also discussed, the invention features stabilized Exendin-4 (1-39) compounds that include at least one of:
i) an Asn residue having a deaminated side chain, an Asn residue having hydrolyzed side chain or a structural isomer of an Asp residue, wherein the Asn or Asp residue corresponds to position 28 of Exendin-4,
ii) an oxidized methionine residue corresponding to position 14 of Exendin-4,
iii) an oxidized tryptophan residue corresponding to position 25 of Exendin-4; and
iv) a deaminated or hydrolyzed Gln corresponding to position 13 of Exendin-4;

and a pharmaceutically acceptable salt or solvate thereof.

Salts and Solvates

Also envisioned are pharmaceutically acceptable salts or solvates of such compounds. Examples of such stabilized Exendin-4 (1-39) compounds include the following sequences:

[Asp$^{28}$]Exendin-4 (1-39) (SEQ ID NO: 83),
[IsoAsp$^{28}$]Exendin-4 (1-39) (SEQ ID NO: 84),

[Cyclic imide$^{28}$]Exendin-4 (1-39) (SEQ ID NO: 85),
[Met(O)$^{14}$]Exendin-4 (1-39) (SEQ ID NO: 86),
[Trp(O$_2$)$^{25}$]Exendin-4 (1-39) (SEQ ID NO: 87),
[Met(O)$^{14}$, Asp$^{28}$]Exendin-4 (1-39) (SEQ ID NO: 88),
[Met(O)$^{14}$, IsoAsp$^{28}$]Exendin-4 (1-39) (SEQ ID NO: 89),
[Met(O)$^{14}$, Cyclic imide$^{28}$]Exendin-4 (1-39) (SEQ ID NO: 90),
[Met(O)$^{14}$, Trp(O$_2$)$^{25}$]Exendin-4 (1-39) (SEQ ID NO: 91),
[Trp(O$_2$)$^{25}$, Asp$^{28}$]Exendin-4 (1-39) (SEQ ID NO: 92),
[Trp(O$_2$), IsoAsp$^{28}$]Exendin-4 (1-39) (SEQ ID NO: 93),
[Trp(O$_2$)$^{25}$, Cyclic imide$^{28}$]Exendin-4 (1-39) (SEQ ID NO: 94),
[Met(O)$^{14}$, Trp(O$_2$)$^{25}$, Asp$^{28}$]Exendin-4 (1-39) (SEQ ID NO: 95),
[Met(O)$^{14}$, Trp(O$_2$)$^{25}$, IsoAsp$^{28}$]Exendin-4 (1-39) (SEQ ID NO: 96), or
[Met(O)$^{14}$, Trp(O$_2$)$^{25}$, Cyclic imide$^{28}$]Exendin-4 (1-39) (SEQ ID NO: 97).

and a pharmaceutically acceptable salt or solvate thereof.

With respect to any of the forgoing stabilized Exendin-4 (1-39) compounds, the compounds may further include a deaminated or hydrolyzed Gln corresponding to position 13 of Exendin-4.

L and D Variants

The stabilized Exendin-4 (1-39) compounds disclosed herein including variants, analogue and derivatives thereof, can feature at least one amino acid in the L- or D-configuration (or both D- and L-forms). In embodiments in which at least one of the amino acid residues is deaminated, the stabilized Exendin-4 (1-39) compound can have at least one amino acid residue in the L-form, at least one amino acid in the D-form, or combinations thereof.

Additionally preferred stabilized Exendin-4 (1-39) compounds and related molecules of the invention feature good biological activity. More preferred are those compounds that exhibit at least 70% of the biological activity of the corresponding unstabilized Exendin-4 (1-39) compound or related molecule, more preferably at least 80%, 90% or greater activity up to about 100% of that biological activity. Methods for testing the biological activity of a variety of Exendin-4 (1-39) compounds and related molecules have been disclosed WO 01/04156 (hereinafter "PCT/DK00/00393"), EP application 99610043.4 and U.S. provisional application 60/143,591, the disclosures of which are incorporated herein by reference.

For example, one acceptable test for Exendin-4 (1-39) biological activity is the blood glucose assay in diabetic ob/ob mice described in the PCT/DK00/00393 application.

It is an object of the invention to provide a pharmaceutically acceptable composition that includes at least one of the stabilized Exendin-4 (1-39) compounds or related molecules disclosed herein. Preferably, such a composition will include less than about 5 compounds, such as two identical compounds.

A wide variety of pharmaceutically acceptable formulations are known in the field and have been disclosed in the PCT/DK00/00393, EP application 99610043.4 and U.S. provisional application 60/143,591.

Formulation

For instance, and as provided in the PCT/DK00/00393 case, an Exendin-4 (1-39) compound or related molecule in accord with the invention can be combined with one or more physiologically acceptable carriers. Such compositions may be in a form adapted to oral, parenteral (including subcutaneous (s.c.), intravenous (i.v.), intramuscular (i.m.), epidural, direct brain and intraperitoneal (i.p.)), rectal, intratracheal, intranasal, dermal, vaginal, buccal, ocularly, or pulmonary administration, preferably in a form adapted to subcutaneous or oral administration, and such compositions may be prepared in a manner well-known to the field. See generally described in "Remington's Pharmaceutical Sciences", 17. Ed. Alfonso R. Gennaro (Ed.), Mark Publishing Company, Easton, Pa., U.S.A., 1985 and more recent editions and in the monographs in the "Drugs and the Pharmaceutical Sciences" series, Marcel Dekker. The compositions may appear in conventional forms, for example, capsules, tablets, aerosols, topical application forms, liquid or semiliquid forms, such as solutions, suspensions, dispersions, emulsions, micelles or liposomes. Preferred are liquid compositions suitable for s.c. administration. In a preferred embodiment, the compositions of the present invention are administered subcutaneously. In an alternative preferred embodiment, the compositions of the present invention are administered orally, and in such cases one preferred administration form is a tablet or capsule.

The pharmaceutical carrier or diluent employed may be a conventional solid or liquid carrier. Examples of solid carriers are lactose, terra alba, sucrose, cyclodextrin, talc, gelatin, agar, pectin, acacia, magnesium stearate, stearic acid or lower alkyl ethers of cellulose. Examples of liquid carriers are syrup, peanut oil, olive oil, phospholipids, sterols, fatty acids, fatty acid amines, polyoxyethylene, isotonic buffer solutions and water. Similarly, the carrier or diluent may include any sustained release material known in the art, such as glyceryl monostearate or glyceryl distearate, alone or mixed with a wax. If a solid carrier is used for oral administration, the preparation may be in the form of a tablet, placed in a hard gelatin capsule in powder or pellet form or it can be in the form of a troche or lozenge. The amount of solid carrier will vary widely but will usually be from about about 25 mg to about 1 g.

A typical tablet, which may be prepared by conventional tabletting techniques may contain:

Core: active compound (as free compound of the invention or salt thereof) 100 mg; colloidal silicon dioxide (Aerosil) 1.5 mg; cellulose, microcryst. (Avicel) 70 mg; modified cellulose gum (Ac-Di-Sol) 7.5 mg; magnesium stearate.

Coating: HPMC approx. 9 mg; *Mywacett 9-40T approx. 0.9 mg; *acylated monoglyceride used as plasticizer for film coating.

If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of the present invention, preferably a conjugate, dissolved or suspended in a liquid carrier, in particular, an aqueous carrier, for aerosol application. The carrier may contain additives such as solubilizing agents, e.g., propylene glycol, surfactants such as bile acid salts or polyoxyethylene higher alcohol ethers, absorption enhancers such as lecithin (phosphatidylcholine) or cyclodextrin, or preservatives such as parabines.

A stabilized Exendin-4 (1-39) compound or related molecule of the invention may also be in a form suited for local or systemic injection or infusion and may, as such, be formulated with sterile water or an isotonic saline or glucose solution. The compositions may be sterilized by conventional sterilization techniques, which are well known in the art. The resulting aqueous solutions may be packaged for use or filtered under aseptic conditions and lyophilized, the lyophilized preparation being combined with the sterile aqueous solution prior to administration. Preferably, the formulation to be used for intravenous, subcutaneous and oral dosing will be a solution of the active compound in buffer. The preparation may be produced immediately before use from active drug substance and sterile buffer solution. One preferred method of sterilization may be by sterile filtration of a solution made immediately prior to use. The compound or related molecule may contain pharmaceutically acceptable auxiliary substances as required to approximate physiological conditions, such as buffering agents, tonicity adjusting agents and the like, for instance sodium acetate, sodium lactate, sodium chloride, potassium chloride, calcium chloride, etc.

The stabilized Exendin-4 (1-39) compounds and related molecules of the invention find use in a wide spectrum of applications. Some are described in WO 99/40788 (relating to the inotropic and diuretic effects of Exendin and GLP-1); and WO 98/39022 (relating to a method of sedating a mammalian subject having increased activation of the central or peripheral nervous system comprising administering Exendin or GLP-1 or an agonist of Exendin or GLP-1 to the subject to produce a sedative or anxiolytic effect on the subject); and WO 93/18786 (relating to the treatment of diabetes using GLP-1(7-37) or GLP-1(7-36)amide in a regimen which additionally comprises treatment with an oral hypoglycaemic agent, such as sulfonylurea, producing a strong synergistic effect); and WO 98/19698 (relating to the use of GLP-1 analogs for the regulation of obesity); WO 98/08531 (relating to the use of GLP-1 or analogs in a method of reducing mortality and morbidity after myocardial infarction); WO 98/08873 (relating to the use of GLP-1 or analogs in a method of attenuating post-surgical catabolic changes and hormonal responses to stress). Besides, the compounds of the invention are suitable in a combination therapy with other antidiabetic agents, such as insulin, metformin, sulfonyl ureas and thiazolidinediones, or in combination therapy with other antiobesity agents, such as leptin, dexphenfluramine, amphetamin etc.

Other formulations are within the scope of the present invention. Such formulations include, but are not limited to, formulations that include at least one of the stabilized Exendin-4 (1-39) compounds disclosed herein combined with liposomes, microspheres and liquid stabilizers. Depot formulations that include at least one of the stabilized Exendin-4 (1-39) compounds are also envisioned. See U.S. Pat. Nos. 5,407,609 and 5,654,008 for additional information.

A particular liquid formulation suitable for use with the present stabilized Exendin-4 (1-39) compounds includes: about 50 mM histidine, about 100 to 200 mM sucrose, mannitol or other acceptable sugar, 20 mM methionine, 20 mM Asparagine-glutamine or Asp, at a pH of about 5.3. The compound can be dissolved in nearly any suitable amount including about 50 micrograms/mL to about 2.5 mg/mL In one embodiment, the pharmaceutically acceptable compositions disclosed herein can include at least one of the following sequences:

des Pro$^{36}$[Asp$^{28}$]Exendin-4 (1-39) (SEQ ID NO: 15),
des Pro$^{36}$[IsoAsp$^{28}$]Exendin-4 (1-39) (SEQ ID NO: 16),
des Pro$^{36}$[Cyclic imide$^{28}$]Exendin-4 (1-39) (SEQ ID NO: 17),
des Pro$^{36}$[Met(O)$^{14}$]Exendin-4 (1-39) (SEQ ID NO: 18),
des Pro$^{36}$[Trp(O$_2$)$^{25}$]Exendin-4 (1-39) (SEQ ID NO: 19),
des Pro$^{36}$[Met(O)$^{14}$, Asp$^{28}$]Exendin-4 (1-39) (SEQ ID NO: 20),
des Pro$^{36}$[Met(O)$^{14}$, IsoAsp$^{28}$]Exendin-4 (1-39) (SEQ ID NO: 21),
des Pro$^{36}$[Met(O)$^{14}$, Cyclic imide$^{28}$]Exendin-4 (1-39) (SEQ ID NO: 22),
des Pro$^{36}$[Met(O)$^{14}$, Trp(O$_2$)$^{26}$]Exendin-4 (1-39) (SEQ ID NO: 23),
des Pro$^{36}$[Trp(O$_2$)$^{25}$, Asp$^{28}$]Exendin-4 (1-39) (SEQ ID NO: 98),
des Pro$^{36}$[Trp(O$_2$)$^{25}$, IsoAsp$^{26}$]Exendin-4 (1-39) (SEQ ID NO: 99),
des Pro$^{36}$[Trp(O$_2$)$^{26}$, Cyclic imide$^{28}$]Exendin-4 (1-39) (SEQ ID NO: 100),
des Pro$^{36}$[Met(O)$^{14}$, Trp(O$_2$)$^{25}$]Exendin-4 (1-39) (SEQ ID NO: 23),
des Pro$^{36}$[Met(O)$^{14}$, Trp(O$_2$)$^{25}$, Asp$^{28}$]Exendin-4 (1-39) (SEQ ID NO: 24),
des Pro$^{36}$[Met(O)$^{14}$, Trp(O$_2$)$^{25}$, IsoAsp$^{28}$]Exendin-4 (1-39) (SEQ ID NO: 25), and
des Pro$^{36}$[Met(O)$^{14}$, Trp(O$_2$)$^{25}$, Cyclic imide$^{28}$]Exendin-4 (1-39) (SEQ ID NO: 26), or a pharmaceutically acceptable salt or solvate thereof.

Each of the specified compounds may optionally include the following group linked to the N- or C-terminus thereof, preferably the C-terminus: -Lys$_6$-NH$_2$ (SEQ ID NO: 106)

Additionally specific pharmaceutically acceptable compositions according to the invention include at least one of the following compounds:

[Asp$^{28}$]Exendin-4 (1-39) (SEQ ID NO: 83),
[IsoAsp$^{28}$]Exendin-4 (1-39) (SEQ ID NO: 84),
[Cyclic imide$^{28}$]Exendin-4 (1-39) (SEQ ID NO: 85),
[Met(O)$^{14}$]Exendin-4 (1-39) (SEQ ID NO: 86),
[Trp(O$_2$)$^{25}$]Exendin-4 (1-39) (SEQ ID NO: 87),
[Met(O)$^{14}$, Asp$^{28}$]Exendin-4 (1-39) (SEQ ID NO: 88),
[Met(O)$^{14}$, IsoAsp$^{28}$]Exendin-4 (1-39) (SEQ ID NO: 89),
[Met(O)$^{14}$, Cyclic imide$^{28}$]Exendin-4 (1-39) (SEQ ID NO: 90),
[Met(O)$^{14}$, Trp(O$_2$)$^{25}$]Exendin-4 (1-39) (SEQ ID NO: 91),
[Trp(O$_2$)$^{25}$, Asp$^{28}$]Exendin-4 (1-39) (SEQ ID NO: 92),
[Trp(O$_2$)$_5$, IsoAsp$^{28}$]Exendin-4 (1-39) (SEQ ID NO: 93),
[Trp(O$_2$)$^{25}$, Cyclic imide$^{28}$]Exendin-4 (1-39) (SEQ ID NO: 94),
[Met(O)$^{14}$, Trp(O$_2$)$^{25}$, Asp$^{28}$]Exendin-4 (1-39) (SEQ ID NO: 95),
[Met(O)$^{14}$, Trp(O$_2$)$^{25}$, IsoAsp$^{28}$]Exendin-4 (1-39) (SEQ ID NO: 96); and
[Met(O)$^{14}$, Trp(O$_2$)$^{25}$, Cyclic imide$^{28}$]Exendin-4 (1-39) (SEQ ID NO: 97)

or a pharmaceutically acceptable salt or solvate thereof.

In one embodiment, the pharmaceutically acceptable composition features a weight ratio of any one of the stabilized Exendin-4 (1-39) compounds or related molecules described herein to Exendin-4 (1-39) or a variant, analogue or derivative thereof being less than about 50% (w/w), less than about 10% (w/w), or in some instances less than about 1% (w/w). An appropriate weight ratio will depend on intended use of the composition and other parameters such as the degree of stability needed.

The present stabilized Exendin-4 (1-39) compositions can be readily made using one or a combination of standard techniques. In one such approach the methods include making/obtaining Exendin-4 (1-39) or a variant, analogue, or derivative thereof; and subsequently exposing or incubating the Exendin-4 (1-39) or the variant, analogue, or derivative thereof under conditions sufficient to introduce at least one of the following amino acids therein:

i) an Asn residue having a deaminated side chain, an Asn residue having hydrolyzed side chain or a structural isomer of an Asp residue, wherein the Asn or Asp residue corresponds to position 28 of Exendin-4, ii) an oxidized methionine residue corresponding to position 14 of Exendin-4,
iii) an oxidized tryptophan residue corresponding to position 25 of Exendin-4,
iv) a deaminated or hydrolyzed Gln corresponding to position 13 of Exendin-4;

and a pharmaceutically acceptable salt or solvate thereof.

Alternatively, the stabilized Exendin-4 (1-39) compounds of the invention can be made by conventional peptide synthetic routes including use of the Merrifield synthesis. Modified amino acid residues in accord with the invention can be purchased from commercial suppliers (eg., modified Gln and Asp) or they can be readily made using standard techniques (eg., oxidation of Met and Trp). See Merrifield, B. (1985) in *Science* 232: 341.

Preferred practice of the methods further include the step of detecting presence or absence of at least one of amino acids (i)-(iv). Preferably also such methods include the step of identifying at least one of the amino acids (i)-(iv) in the composition.

Suitable methods for detecting the stabilized Exendin-4 (1-39) compositions and related molecules disclosed herein are known in the field and include, but are not limited to, reverse phase high performance liquid chromatography (RP-HPLC), and liquid chromatography/mass spectrometry (LC-MS). Additionally suitable techniques include conventional amino acid sequencing, peptide mapping, MS/MS and fluorescence.

In another aspect, the invention provides a method of making the pharmaceutically acceptable compositions that include stabilized Exendin-4 compositions or related molecules. In one embodiment, the method includes at least one of the following steps:
a) obtaining Exendin-4 (1-39) or a variant, analogue or derivative thereof,
b) contacting the Exendin-4 (1-39) or the variant, analogue or derivative with at least one pharmaceutically acceptable carrier or vehicle to produce a mixture; and
c) incubating the mixture under conditions sufficient to introduce at least one of the following amino acids therein:
   i) an Asn residue having a deaminated side chain, an Asn residue having hydrolyzed side chain or a structural isomer of an Asp residue, wherein the Asn or Asp residue corresponds to position 28 of Exendin-4,
   ii) an oxidized methionine residue corresponding to position 14 of Exendin-4,
   iii) an oxidized tryptophan residue corresponding to position 25 of Exendin-4
   iv) a deaminated or hydrolyzed Gln corresponding to position 13 of Exendin-4;

and a pharmaceutically acceptable salt or solvate thereof.

Preferred practice of the methods further include the step of detecting presence or absence of at least one of amino acids (i)-(iv). Preferably also such methods include the step of identifying at least one of the amino acids (i)-(iv) in the composition.

Typical conditions for making the stabilized Exendin-4 (1-39) compounds and related molecules will be generally sufficient to introduce at least one of the foregoing amino acid modifications (i)-(iii) as described above. Such conditions are preferably also capable of modifying the glutamine position 13 in the Exendin-4 molecule. Examples of such conditions include, but are not limited to, exposure to water, buffer, heat, water vapor, oxygen, light, metals and metal ions. Such conditions can include contact with a variety of temperatures including contact with about 1° C. up to about 80° C., preferably 5° C. to about 45° C. Room temperature (25° C.) is generally preferred for some applications. Air has been found to be particularly good at modifying the amino acid residues of the Exendin-4 molecule.

However as discussed, it will often be generally preferred to make the stabilized Exendin-4 (1-39) molecules by a synthetic or semi-synthetic approach. A preferred example of such a strategy is use of the Merrifield peptide synthesis procedure in an automated format.

As discussed, the invention further provides a method of stabilizing Exendin-4 (1-39) or a variant, analogue or derivative thereof from degradation before, during or after intended use. Typical methods include at least one of the following steps:
a) obtaining Exendin-4 (1-39) or a variant, derivative or analogue thereof; and
b) incubating the Exendin-4 (1-39) or the variant, derivative or analogue under conditions sufficient to introduce at least one of the following amino add residues therein:
   i) an Asn residue having a deaminated side chain, an Asn residue having hydrolyzed side chain or a structural isomer of an Asp residue, wherein the Asn or Asp residue corresponds to position 28 of Exendin-4,
   ii) an oxidized methionine residue corresponding to position 14 of Exendin-4,
   iii) an oxidized tryptophan residue corresponding to position 25 of Exendin-4
   iv) a deaminated or hydrolyzed Gln corresponding to position 13 of Exendin-4;

and a pharmaceutically acceptable salt or solvate thereof.

For instance, the method conditions include contact with at least one of water, heat, water vapor, light metal, metal ion or oxygen. Such conditions can include contact with a variety of temperatures including contact with about 1° C. up to about 80° C., preferably 5° C. to about 45° C. Room temperature (25° C.) is generally preferred for some applications.

Also preferably, the method includes the step of identifying at least one of the amino acids (i)-(iv) in the stabilized Exendin-4 (1-39) or variant, analogue or derivative thereof. Optionally, the method may further include contacting the stabilized Exendin-4 (1-39) or variant, derivative or analogue thereof with at least one pharmaceutically acceptable carrier or vehicle.

As discussed, many suitable Exendin-4 and related compounds have been disclosed PCT/DK00/00393, EP application 99610043.4 and U.S. provisional application 60/143, 591.

As disclosed in the PCT/DK00/00393 application, one type of Exendin-4 compound is directed to a peptide conjugate comprising a peptide X selected from the group consisting of
(a) an Exendin having at least 90% homology to Exendin-4;
(b) a variant of said Exendin wherein said variant comprises a modification selected from the group consisting of between one and five deletions at positions 34-39 and contains a Lys at position 40 having a lipophilic substituent; or
(c) GLP-1 (7-36) or GLP-1 (7-37) having at least one modification selected from the group consisting of:
   (i) substitution of D-alanine, glycine or alpha-amino isobutyric acid for alanine at position 8 and
   (ii) a lipophilic substituent,
   and Z, a peptide sequence of 4-20 amino acid units covalently bound to said variant, wherein each amino acid unit in said peptide sequence, Z is selected from the group consisting of Ala, Leu, Ser, Thr, Tyr, Asn, Gln, Asp, Glu, Lys, Arg, His, Met, Orn, and amino acid units of the general formula I

$$-NH-C(R^1)(R^2)-C(=O)- \qquad (I)$$

wherein $R^1$ and $R^2$ are selected from the group consisting of hydrogen, $C_{1-6}$-alkyl, phenyl, and phenyl-methyl, wherein $C_{1-6}$-alkyl is optionally substituted with from one to three substituents selected from halogen, hydroxy, amino, cyano, nitro, sulfono, and carboxy, and phenyl and phenyl-methyl is optionally substituted with from one to three substituents selected from $C_{1-6}$-alkyl, $C_{2-6}$alkenyl, halogen, hydroxy, amino, cyano, nitro, sulfono, and carboxy, or $R^1$ and $R^2$ together with the carbon atom to which they are bound form a cyclopentyl, cyclohexyl, or cycloheptyl ring, e.g. 2,4-diaminobutanoic acid and 2,3-diaminopropanoic acid, with the proviso that X is not Exendin-4 or Exendin-3.

The peptide X is further characterised in being effective in improving glucose tolerance in a diabetic mammal.

Furthermore, the PCT/DK00/00393 application features a novel variant of a parent Exendin, wherein said parent Exendin has an amino acid sequence having at least an 90% homology to Exendin-4 and wherein said variant lowers the blood glucose level in a mammal, binds to a GLP-1 receptor and has at least one modification selected from the group consisting of (a) between one and five deletions at positions 34-38, and (b) contains a Lys at position 40 having a lipophilic substituent attached to the epsilon amino group of said lysine.

By the phrase "Exendin variant" is meant a variant of a parent Exendin peptide having at least about 90% homology, more preferably at least about 95% homology to Exendin-4, which have Exendin activity, e.g., lowers the blood glucose level in a mammal and binds to a GLP-1 receptor. In a preferred embodiment the parent Exendin peptide has an amino acid sequence which differs by five amino acids, preferably by four amino acids, more preferably by three amino acids, even more preferably by two amino acids, and still more preferably by one amino acid residue from the amino acid sequence of Exendin-4 (1-39). See the PCT/DK00/00393 application for additional information.

Additionally suitable Exendin-4 variants, analogues and derivatives thereof have been disclosed in the following references, each of which is individually incorporated by reference: U.S. Pat. Nos. 6,358,924; 6,344,180; 6,284,725; 6,277,819; 6,271,241; 6,268,343; 6,191,102; 6,051,689; 6,006,753; 5,846,937; 5,670,360; 5,614,492; 5,846,937; 5,545,618; 6,410,508; 6,388,053; 6,384,016; 6,329,336; 6,110,703; 5,846,747; 5,670,360; 5,631,224; 5,424,286; WO98/05351; WO98/30231; WO99/07404, WO 99/25727; WO 99/25728; or WO 99/46283. Each of said compounds can be stabilized in accord with this invention eg., by exposing the compounds to the stabilizing conditions disclosed herein. Alternatively, such stabilized Exendin-4 (1-39) compounds can be made synthetically using the Merrifield synthesis and starting materials that can be purchased or readily made.

It should be understood that the compositions and compounds of the invention might also be in the preferred amide ($NH_2$) or in the free acid (OH) form or in the form of a salt thereof.

In embodiments in which one or more of the stabilized Exendin-4 (1-39) compounds and related molecules are used therapeutically, such use will typically involve administration of one or more of the pharmaceutically acceptable compositions disclosed herein. Such a composition can be combined with at least one of Exendin-4, Exendin-3, or derivatives, analogs or variants thereof together with a suitable amount of vehicle and/or stabilizer. In one embodiment, such an approach involves administering the composition (eg. as a depot formulation, liquid formulation, with microspheres or liposomes, i.v) to provide a dosage of about 0.1 pg/kg, to 1.000 mg/kg body weight. The amount of the composition to use will depend on recognized parameters including age, severity of the disease, total body weight, sex and other factors.

A "peptide" as used herein is any compound produced by amide formation between a carboxyl group of one amino acid and an amino group of another. The amide bonds in peptides may be called peptide bonds. The word peptide usually applies to compounds whose amide bonds are formed between C—I of one amino acid and N-2 of another (sometimes called eupeptide bonds), but it includes compounds with residues linked by other amide bonds (sometimes called isopeptide bonds). Peptides with fewer than about 10-20 residues may also be called oligopeptides and peptides with more than 20 residues are called polypeptides. Polypeptides of specific sequences of more than about 50 residues are usually known as proteins. A "natural polypeptide sequence" as used herein refers to a polypeptide sequence consisting of natural L-amino acid residues and which is capable of being expressed by a recombinant host cell. The X compounds herein are all peptide sequences of 40 amino acid residues or less.

"GLP-1" as used herein includes GLP-1(7-37)-OH, GLP-1(7-37)-$NH_2$, GLP-1(7-36)-OH, and GLP-1(7-36)-$NH_2$.

Molecules are "related" to Exendin-4 if they are recognized analogues, derivatives, or variants thereof as described herein and in the PCT/DK00/00393, EP application 99610043.4, and U.S. provisional application 60/143,591. Other such molecules have been disclosed in the following U.S patent applications: U.S. Pat. Nos. 6,358,924; 6,344,180; 6,284,725; 6,277,819; 6,271,241; 6,268,343; 6,191,102; 6,051,689; 6,006,753; 5,846,937; 5,670,360; 5,614,492; 5,846,937; 5,545,618; 6,410,508; 6,388,053; 6,384,016; 6,329,336; 6,110,703; 5,846,747; 5,670,360; 5,631,224. 5,424,286; WO98/05351; WO98/30231; WO99/07404, WO 99/25727; WO 99/25728; and WO 99/46283, for example.

"Agonist" refers to an endogenous substance or a drug that can interact with a receptor and initiate a physiological or a pharmacological response characteristic of that receptor (contraction, relaxation, secretion, enzyme activation, etc.).

"Antagonist" refers to a drug or a compound that opposes the physiological effects of another. At the receptor level, it is a chemical entity that opposes the receptor-associated responses normally induced by another bioactive agent.

"Partial agonist" refers to an agonist, which is unable to induce maximal activation of a receptor population, regardless of the amount of drug applied. A "partial agonist" may be termed "agonist with intermediate intrinsic efficacy" in a given tissue. Moreover, a partial agonist may antagonize the effect of a full agonist that acts on the same receptor.

"Receptor" refers to a molecule or a polymeric structure in or on a cell that specifically recognizes and binds a compound acting as a molecular messenger (neurotransmitter, hormone, lymphokine, lectin, drug, etc.).

By "Exendin variant" of the present invention is to be understood a variant of a parent Exendin peptide having at least about 90% homology to Exendin-4 and most preferably having at least about 95% homology to Exendin-4 (1-39), which has Exendin activity, e.g., lowers the blood glucose level in a mammal and binds to a GLP-1 receptor, "Exendin-4" as used herein refers to Exendin-4 (1-39) the amino acid sequence of which is disclosed in U.S. Pat. No. 5,424,286, SEQ ID NO:2, and Exendin-4 (1-40) as disclosed by Chen &

Drucker in The Journal of Biological Chemistry, Vol. 272, No. 7, pp. 4108-15 which differs only in having glycine in position 40 as C-terminal amino acid residue. The homology of the parent Exendin is determined as the degree of identity between two protein sequences indicating a derivation of the first sequence from the second. The homology may suitably be determined by means of computer programs known in the art such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), J. Mol. Biol. 48:443-453). The following settings for polypeptide sequence comparison may be used: GAP creation penalty of 3.0 and GAP extension penalty of 0.1.

By "Met(O)" of the present invention is intended to mean a methionine sulfoxide or methionine sulfone.

By "Trp($O_2$)" of the present invention is intended to mean N-formylkynurenine, a tryptophan residue that has undergone dioxidation.

"Salts" include pharmaceutically acceptable salts, such as acid addition salts and basic salts. Examples of acid addition salts are hydrochloride salts, sodium salts, hydrobromide salts, etc. Examples of basic salts are salts where the cation is selected from alkali metals, such as sodium and potassium, alkaline earth metals, such as calcium, and ammonium ions $^+N(R^3)_3(R^4)$, where $R^3$ and $R^4$ independently designates optionally substituted $C_{1-6}$-alkyl, optionally substituted $C_{2-6}$-alkenyl, optionally substituted aryl, or optionally substituted heteroaryl. Other examples of pharmaceutically acceptable salts are; e.g., those described in "Remington's Pharmaceutical Sciences" 17. Ed. Alfonso R. Gennaro (Ed.), Mark Publishing Company, Easton, Pa., U.S.A., 1985 and more recent editions, and in Encyclopedia of Pharmaceutical Technology.

Single and triple letter designations for the amino acids are used interchangeably. For example, it will be appreciated that Lys and K refer to lysine, Asp and D refer to aspartic acid, Glu and E refer to glutamic acid, ect. A complete description of the amino acid designations can be found in Alberts, B. et al. in *Molecular Biology of the Cell*, $2^{nd}$ Ed. Garland Publishing, Inc. (New York) (1989).

The following Examples are illustrative and not limiting as to the scope of the present invention.

EXAMPLE 1

Stabilization of Exendin-4 and Related Molecules by Structural Isomerization and/or Oxidation Pharmaceutical compositions of Exendin-4 (1-39) or a variant, analogue, or derivative thereof or aqueous solutions of Exendin-4 (1-39) or a variant, analogue, or derivative thereof can be stabilized by oxidation or functional isomerization at various points in the Exendin-4 (1-39) sequence.

Storage of the Exendin-4 (1-39) or a variant, analogue, or derivative thereof in an aqueous solution at a temperature of between about 0° C. and about 50° C., more particularly between about 4° C. and room temperature can induce a structural rearrangement at the 28-L-Asparaginyl residue of the Exendin-4 (1-39) peptide. Suitable aqueous solutions are not particularly limited and may include aqueous pharmaceutical compositions which may have one or more additional additives to facilitate administration to a patient or to stabilize or solubilize the Exendin-4 (1-39) or a variant, analogue, or derivative thereof.

Although not bound by theory, one synthetic pathway through which the structural rearrangement of the 28-L-Asparaginyl residue (structure A) may occur is presented in Synthetic Scheme 1. The 28-L-Asparaginyl residue undergoes deamination in aqueous media to form a Cyclic imide residue, which is depicted as (structure B). Reversible hydrolysis of the Cyclic imide leads to formation of both L-aspartyl residue (structure C) or a L-isoAspartyl residue (structure D). Each hydrolysis reaction is reversible such that one or more stabilized Exendin compounds having the 28-Cyclic imide residue, 28-L-aspartyl residue or 28-L-isoAspartyl residue may be present in the aqueous solution.

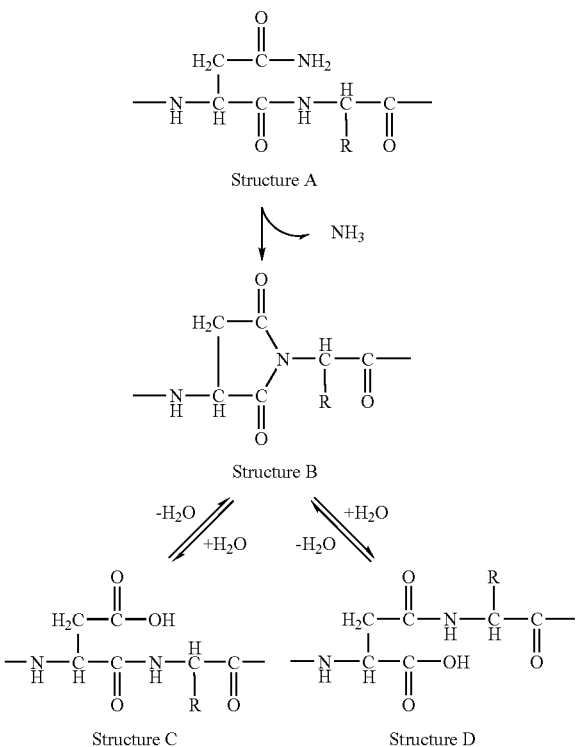

Synthetic Scheme 1

Oxidation products are formed by incubating an aqueous solution of Exendin-4 (1-39) or an Exendin-4 (1-39) compound in the presence of an oxidant such as dioxygen.

Typically pharmaceutical compositions of the present invention, which are exposed to molecular dioxygen during processing, or storage are susceptible to oxidation of the 14-methionine or 25tryptophan residues.

One non-limiting route to oxidation of the 14-methionine residue occurs upon oxidation In the presence of molecular dioxygen. A 14-methionine sulfoxide is produced by reaction of Exendin-4 (1-39) in aqueous solution with half an equivalent of molecular dioxygen. Further exposure of the stabilized Exendin compound having a 14-methionine sulfoxide results in formation of 14-methionine sulfone in which the 14-methionine residue has been oxidized by one equivalent of dioxygen.

The 25-tryptophan residue of Exendin-4 (1-39) or an Exendin-4 (1-39) variant, analogue, or derivative may be oxidized by 0.5, 1, 1.5, 2 or more equivalents of molecular dioxygen. Common oxidized tryptophan products include hydroxytryptophan, N-formylkynuranine, kynuranine, and 3-hydroxykynuranine. Under normal storage or incubation conditions of about 0° C. to about 25° C., one equivalent of molecular dioxygen oxidizes the 25-tryptophan residue of Exendin-4

(1-39) or an Exendin-4 (1-39) variant to form an Exendin-4 (1-39) compound having a 25-N-formylkynuranine residue.

EXAMPLE 2

Synthesis of Compound 5, 6 and 14 (Stabilized Derivatives of Compound 1)

Compound 1 (des Pro$^{36}$ Exendin-4 (1-39)-K$_6$) (SEQ ID NO: 1) has the structure shown in FIG. 1 and it was made using the Merrifield technique. See the PCT/DK00/00393 application, for example, for more information.

About 458 mg of Compound 1 was dissolved in 100 mM NH$_4$HCO$_3$ pH 7.9 to a concentration of 10 mg/mL. The solution was incubated at 40° C. for 6 days to yield approx. 20% Compound 5, 10% Compound 14 and 50% Compound 6.

The stabilized product Compound 5 and Compound 6 can be purified by preparative RP-HPLC isocratic elution or using a gradient, respectively. Identification is accomplished by relative retention time in combination with Amino acid Sequencing and LC-MS (ESI$^+$/TOF)

EXAMPLE 3

Synthesis of a Compound 7 (Stabilized Derivative of Compound 1)

About 424 mg of Compound 1 was dissolved in 100 mM NH$_4$HCO$_3$ pH 7.9 to a concentration of 10 mg/mL. The solution was incubated at 40° C. for 5 days to yield approx. 20% Compound 5, 60% Compound 6. Compound 6 was purified by preparative RP-HPLC. Approximately 100 mg Compound 6 was obtained and lyophilised. About 100 mg Compound 6 was reconstituted in 100 mM NaH$_2$PO$_4$ buffer and adjusted to pH 5.3 with NaOH to a concentration of 5 mg/mL. The solution was incubated at 40° C. for 5 days to yield approximately 40% Compound 7.

The stabilized product Compound 7 can be purified by preparative RP-HPLC gradient elution. Identification is accomplished by relative retention time in combination with LC-MS (ESI$^+$/TOF).

EXAMPLE 4

Synthesis of Compounds 3 and 4 (a Stabilized Derivative of Compound 1)

Compound 1 was made as described. It was dissolved (10 mg) in 50 mM citrate buffer containing 3% (w/v) D-mannitol to a concentration of 100 µg/mL. The solution was incubated at 25° C. for at least 6 days and exposed to light 350 nm mean wavelength.

The stabilized products Compound 3 and 4 can be purified by preparative RP-HPLC. Identification is accomplished by relative retention time in combination with peptide mapping by LC-MS (ESI$^+$/TOF) of a tryptic digest and MS/MS plus flourescence detection.

EXAMPLE 5

Synthesis of Compound 2 (Stabilized Derivative of Compound 1)

Compound 1 was made as described. It was dissolved (100 mg) in 10 mL pure water to a concentration of 10 mg/mL and exposed to H$_2$O$_2$ by adding 2.3 mL of 3.5% H$_2$O$_2$. The solution was incubated at 25° C. for 1 day to yield approx. 100% Compound 2.

The stabilized product Compound 2 can be purified by preparative RP-HPLC. Identification is accomplished by relative retention time in combination with peptide mapping by LC-MS (ESI$^+$/TOF) of a tryptic digest and MS/MS plus flourescence detection.

EXAMPLE 6

Peptide Synthesis

Peptide synthesis of Compound 8, H-His-Gly-Glu-Gly-Thr-Phe-Thr-Ser-Asp-Leu-Ser-Lys-Glu-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$ (SEQ ID NO: 8) ([Glu$^{13}$]Exendin-4-NH$_2$ (SEQ ID NO: 8) on TentaGel S-RAM.

Dry TentaGel S-RAM resin (0.23 mmol/g, 1.0 g) is placed in a polyethylene vessel equipped with a polypropylene filter for filtration and swelled for two hours in DMF (5 ml). The Fmoc group is removed according to the procedure described above, and the peptide according to the sequence is assembled as described under "Batchwise peptide synthesis on TentaGel S-RAM resins [Due Larsen, B. and Holm, A. (1998) J. Pept. Res. 52, 470]. After completion of the synthesis, the peptide-resin is washed with DMF (3×5 ml, 1 min each), DCM (3×5 ml, 1 min each), diethyl ether (3×5 ml, 1 min each) and dried in vacuo. The peptide is cleaved from the resin by treatment with 95% trifluoroacetic acid and 5% ethanedithiol v/v at r.t. for 2 h. The filtered resins are washed with 95% TFA-water and filtrates and washings are diluted by adding water. The resulting mixture is extracted 3 times with ether and finally freeze dried. The crude peptide is purified by preparative HPLC. The purified product was found to be homogeneous and the purity was found to be better than 95%. The identity of the peptide was confirmed by ES-MS (Mw found 4185.17 and calculated 4185.01).

Peptide synthesis of Compound 9, H-His-Gly-Glu-Gly-Thr-Phe-Thr-Ser-Asp-Leu-Ser-Lys-Glu-Met-Glu-Glu-Glu-Ala-Val-Arg-Leu-Phe-Ile-Glu-Trp-Leu-Lys-Asp-Gly-Gly-Pro-Ser-Ser-Gly-Ala-Pro-Pro-Pro-Ser-NH$_2$ (SEQ ID NO: 9) ([Glu$^{13}$,Asp$^{28}$]Exendin-4-NH$_2$ (SEQ ID NO: 9)) on TentaGel S-RAM.

Dry TentaGel S-RAM resin (0.23 mmol/g, 1.0 g) is placed in a polyethylene vessel equipped with a polypropylene filter for filtration and swelled for two hours in DMF (5 ml). The Fmoc group is removed according to the procedure described above, and the peptide according to the sequence is assembled as described under "Batchwise peptide synthesis on TentaGel S-RAM resins [Due Larsen, B. and Holm, A. (1998) J. Pept. Res. 52, 470]. After completion of the synthesis, the peptide-resin is washed with DMF (3×5 ml, 1 min each), DCM (3×5 ml, 1 min each), diethyl ether (3×5 ml, 1 min each) and dried in vacuo. The peptide is cleaved from the resin by treatment with 95% trifluoroacetic acid and 5% ethanedithiol v/v at r.t. for 2 h. The filtered resins are washed with 95% TFA-water and filtrates and washings are diluted by adding water. The resulting mixture is extracted 3 times with ether and finally freeze dried. The crude peptide is purified by preparative HPLC. The purified product was found to be homogeneous and the purity was found to be better than 95%. The identity of the peptide was confirmed by ES-MS (Mw found 4186.25 and calculated 4186.18).

Peptide synthesis of Compound 10, H-His-Gly-Glu-Gly-Thr-Phe-Thr-Ser-Asp-Leu-Ser-Lys-Gln-Met-Glu-Glu-Glu- Ala-Val-Arg-Leu-Phe-Ile-Glu-Trp-Leu-Lys-Asp-Gly-Gly-Pro-Ser-Ser-Gly-Ala-Pro-Pro-Pro-Ser-NH$_2$ (SEQ ID NO: 10) ([Asp$^{28}$]Exendin-4-NH$_2$ (SEQ ID NO: 10)) on TentaGel S-RAM.

Dry TentaGel S-RAM resin (0.23 mmol/g, 1.0 g) is placed in a polyethylene vessel equipped with a polypropylene filter for filtration and swelled for two hours in DMF (5 ml). The Fmoc group is removed according to the procedure described above, and the peptide according to the sequence is assembled as described under "Batchwise peptide synthesis on TentaGel S-RAM resins [Due Larsen, B. and Holm, A. (1998) J. Pept. Res. 52, 470]. After completion of the synthesis, the peptide-resin is washed with DMF (3×5 ml, 1 min each), DCM (3×5 ml, 1 min each), diethyl ether (3×5 ml, 1 min each) and dried in vacuo. The peptide is cleaved from the resin by treatment with 95% trifluoroacetic acid and 5% ethanedithiol v/v at r.t. for 2 h. The filtered resins are washed with 95% TFA-water and filtrates and washings are diluted by adding water. The resulting mixture is extracted 3 times with ether and finally freeze dried. The crude peptide is purified by preparative HPLC. The purified product was found to be homogeneous and the purity was found to be better than 95%. The identity of the peptide was confirmed by ES-MS (Mw found 4185.38 and calculated 4185.01).

Peptide synthesis of Compound 11, H-His-Gly-Glu-Gly-Thr-Phe-Thr-Ser-Asp-Leu-Ser-Lys-Glu-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH$_2$ (SEQ ID NO: 11) (des Pro$^{36}$-[Glu$^{13}$]Exendin-4-(Lys)$_6$-NH$_2$ (SEQ ID NO: 11)) on TentaGel S-RAM.

Dry TentaGel S-RAM resin (0.23 mmol/g, 1.0 g) is placed in a polyethylene vessel equipped with a polypropylene filter for filtration and swelled for two hours in DMF (5 ml). The Fmoc group is removed according to the procedure described above, and the peptide according to the sequence is assembled as described under "Batchwise peptide synthesis on TentaGel S-RAM resins [Due Larsen, B. and Holm, A. (1998) J. Pept. Res. 52, 470]. After completion of the synthesis, the peptide-resin is washed with DMF (3×5 ml, 1 min each), DCM (3×5 ml, 1 min each), diethyl ether (3×5 ml, 1 min each) and dried in vacuo. The peptide is cleaved from the resin by treatment with 95% trifluoroacetic acid and 5% ethanedithiol v/v at r.t. for 2 h. The filtered resins are washed with 95% TFA-water and filtrates and washings are diluted by adding water. The resulting mixture is extracted 3 times with ether and finally freeze dried. The crude peptide is purified by preparative HPLC. The purified product was found to be homogeneous and the purity was found to be better than 95%. The identity of the peptide was confirmed by ES-MS (Mw found 4855.72 and calculated 4855.52).

Peptide synthesis of Compound 12, H-His-Gly-Glu-Gly-Thr-Phe-Thr-Ser-Asp-Leu-Ser-Lys-Gln-Met(O)-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH$_2$ (SEQ ID NO: 12) (des Pro$^{36}$-[Met(O)$^{14}$]Exendin-4-(Lys)$_6$-NH$_2$ (SEQ ID NO: 12)) on TentaGel S-RAM.

Dry TentaGel S-RAM resin (0.23 mmol/g, 1.0 g) is placed in a polyethylene vessel equipped with a polypropylene filter for filtration and swelled for two hours in DMF (5 ml). The Fmoc group is removed according to the procedure described above, and the peptide according to the sequence is assembled as described under "Batchwise peptide synthesis on TentaGel S-RAM resins [Due Larsen, B. and Holm, A. (1998) J. Pept. Res. 52, 470]. The Methionine sulfoxide was incorporated as Fmoc-Met(O)—OH (Purchased from Bachem) according to the described coupling procedures [Due Larsen, B. and Holm, A. (1998) J. Pept. Res. 52, 470]. After completion of the synthesis, the peptide-resin is washed with DMF (3×5 ml, 1 min each), DCM (3×5 ml, 1 min each), diethyl ether (3×5 ml, 1 min each) and dried in vacuo. The peptide is cleaved from the resin by treatment with 95% trifluoroacetic acid and 5% ethanedithiol v/v at r.t. for 2 h. The filtered resins are washed with 95% TFA-water and filtrates and washings are diluted by adding water. The resulting mixture is extracted 3 times with ether and finally freeze dried. The crude peptide is purified by preparative HPLC. The purified product was found to be homogeneous and the purity was found to be better than 95%. The identity of the peptide was confirmed by ES-MS (Mw found 4870.88 and calculated 4870.53).

Peptide synthesis of Compound 13, H-His-Gly-Glu-Gly-Thr-Phe-Thr-Ser-Asp-Leu-Ser-Lys-Gln-Met(O$_2$)-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH$_2$ (SEQ ID NO: 13). (des Pro$^{36}$-[Met(O$_2$)$^{14}$]Exendin-4-(Lys)$_6$-NH$_2$ (SEQ ID NO: 13)) on TentaGel S-RAM.

Dry TentaGel S-RAM resin (0.23 mmol/g, 1.0 g) is placed in a polyethylene vessel equipped with a polypropylene filter for filtration and swelled for two hours in DMF (5 ml). The Fmoc group is removed according to the procedure described above, and the peptide according to the sequence is assembled as described under "Batchwise peptide synthesis on TentaGel S-RAM resins [Due Larsen, B. and Holm, A. (1998) J. Pept. Res. 52, 470]. The Methionine sulfone was incorporated as Fmoc-Met(O$_2$)—OH (Purchased from Bachem) according to the described coupling procedures [Due Larsen, B. and Holm, A. (1998) J. Pept. Res. 52, 470]. After completion of the synthesis, the peptide-resin is washed with DMF (3×5 ml, 1 min each), DCM (3×5 ml, 1 min each), diethyl ether (3×5 ml, 1 min each) and dried in vacuo. The peptide is cleaved from the resin by treatment with 95% trifluoroacetic acid and 5% ethanedithiol v/v at r.t. for 2 h. The filtered resins are washed with 95% TFA-water and filtrates and washings are diluted by adding water. The resulting mixture is extracted 3 times with ether and finally freeze dried. The crude peptide is purified by preparative HPLC. The purified product was found to be homogeneous and the purity was found to be better than 95%. The identity of the peptide was confirmed by ES-MS (Mw found 4886.68 and calculated 4886.53).

Oral Glucose Tolerance Test (OGTT)

The anti diabetic effect of the present compounds was tested in an oral glucose tolerance test (OGTT). In short, animals were fasted over night, and blood samples were taken from the tip of the tail and the blood glucose measured. The whole blood glucose (mM) concentration was analysed by the immobilised glucose oxidase method using a drop of blood (<5 µl; Elite Autoanalyser, Bayer, Denmark) following the manufacturer's manual. The animals were kept fasted throughout the test. Immediately after the initial blood sample (fasting blood glucose level) test compound or vehicle was administered i.p. Fifteen minutes later an oral dose of glucose ((1 g/kg) Sigma, St. Louis, Mo., U.S.A.)), dissolved in phosphate buffer (pH=7.40) was given, and the animals were returned to their home cages (time=0). Blood glucose (BG) levels were measured at time=30 min, time=60 min and time=120 min for Compound 1, 8, 9, 10 and 11 and additionally time=240 min for Compounds 1, 2, 5, 6, 7 and 14. To analyse the effects of the test compounds on oral glucose tolerance the absolute difference in BG from baseline (fasting BG) was calculated for each time point. The area under the curve (AUC) (FIG. 1-8) for the whole experiment (AUC$_{0-120\ min}$) or (AUC$_{0-240\ min}$) was determined using the trapezoid method. Before starting the experimental series an OGTT was used to stratify animals into groups of 9-10 animals displaying similar glucose tolerances in all groups. Animals displaying excessive glucose excursion 30 min after glucose loading (BG>33 mmol/l) were excluded from the study.

Results of the Glucose Tolerance Test

The results of the glucose tolerance test are illustrated in the FIGS. 1-4. The calculated ED$_{50}$ values are presented in Table 1.

TABLE 1

| Major Compound in Test Solution | ED$_{50}$ (nmol/kg) | SD$_r$ |
|---|---|---|
| Compound 1 | 0.049 | 3.8 |
| Compound 14 | 0.55 | 1.3 |
| Compound 6 | 0.013 | 19 |
| Compound 7 | 0.21 | 2.1 | shows the ED$_{50}$ based on curve fits and the standard deviation ratio (SD$_r$).

The fit of the data obtained after treatment with Compound 1 is illustrated in FIG. 1. The calculated ED$_{50}$ and SD$_r$ is shown in Table 1.

Figure 2:
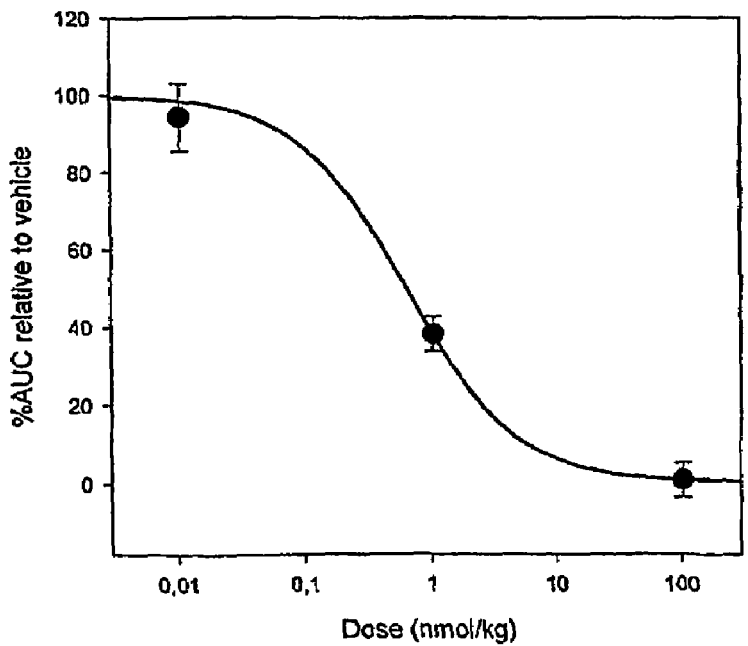
FIG. 2 shows the effect of Compound 14 on glucose tolerance in mice.

The fit of the data obtained after treatment with Compound 14 is illustrated in FIG. 2. The calculated ED$_{50}$ and SD$_r$ is shown in Table 1.

Figure 3:
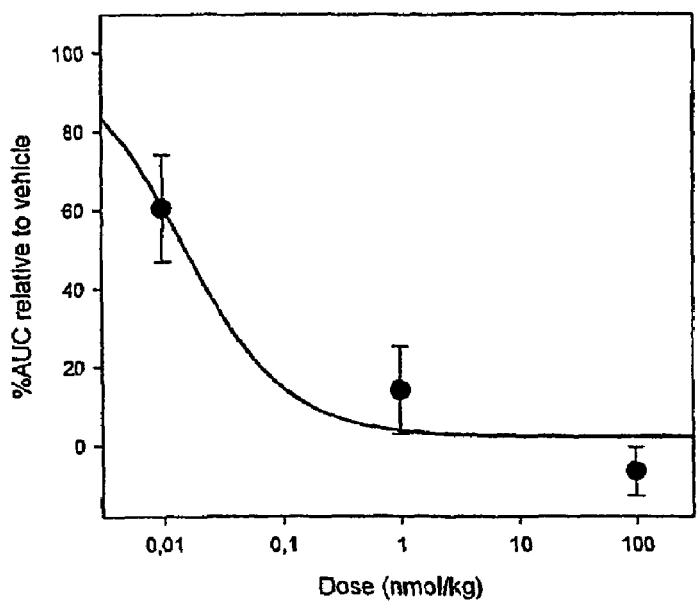
FIG. 3 shows the effect of Compound 6 on glucose tolerance in mice.

The fit of the data obtained after treatment with Compound 6 is illustrated in FIG. 3. The calculated ED$_{50}$ and SD$_r$ is shown in Table 1.

Figure 4:
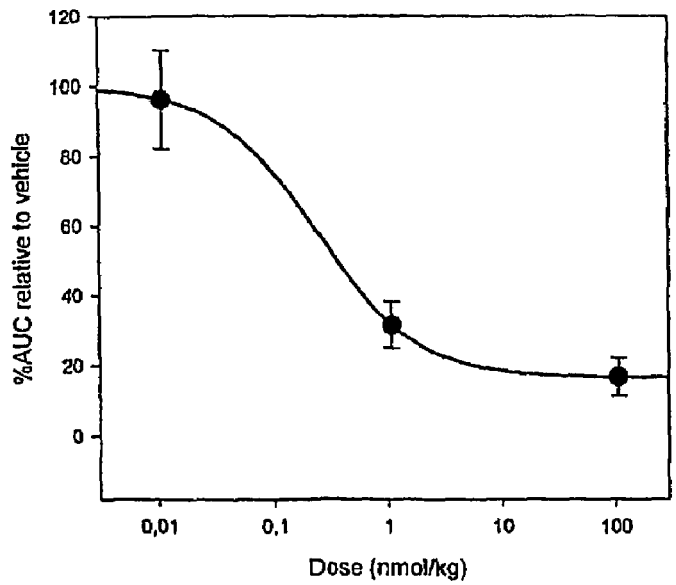
FIG. 4 shows the effect of Compound 7 on glucose tolerance in mice.

The fit of the data obtained after treatment with Compound 7 is illustrated in FIG. 4. The calculated ED$_{50}$ and SD$_r$ is shown in Table 1.

Figure 5:
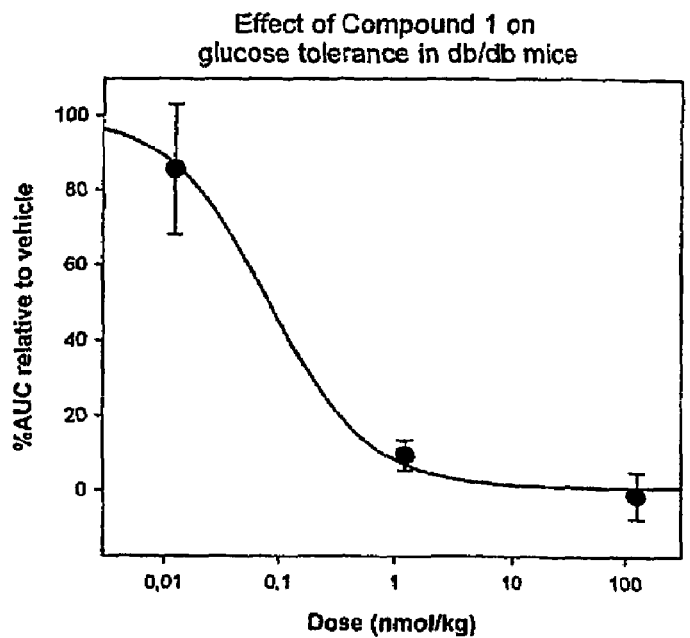
FIG. 5 shows the effect of Compound 1 on glucose tolerance in mice.
Figure 6:
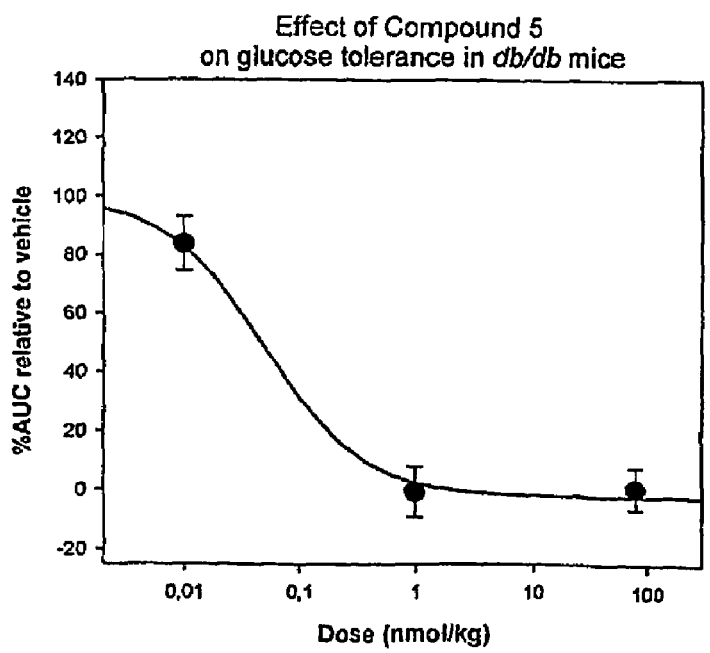
FIG. 6 shows the effect of Compound 5 on glucose tolerance in mice.
Figure 7:
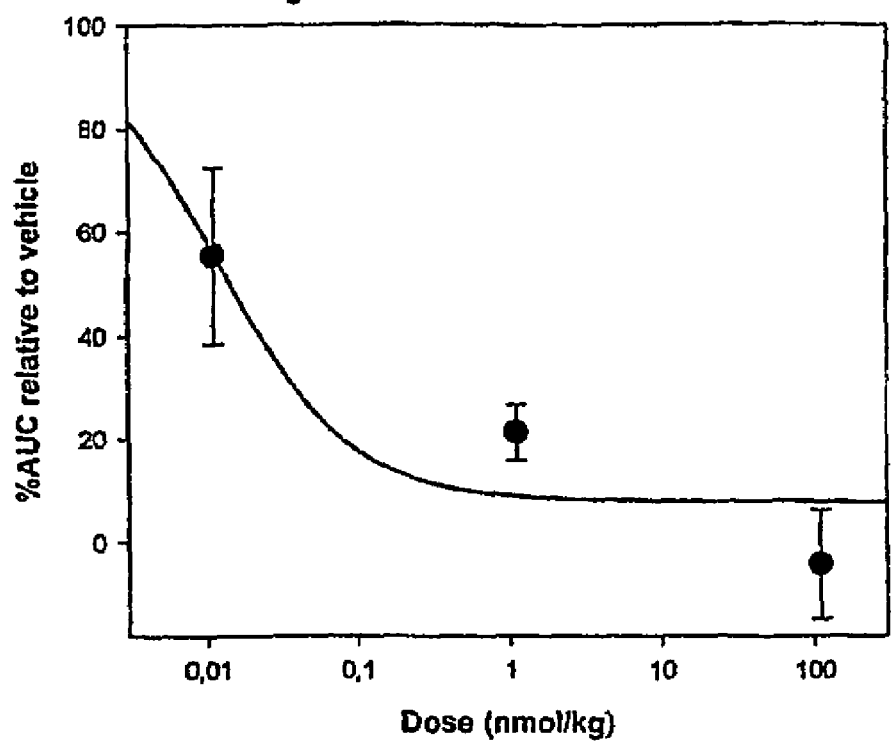
FIG. 7 shows the effect of Compound 2 on glucose tolerance in mice.
Figure 8:
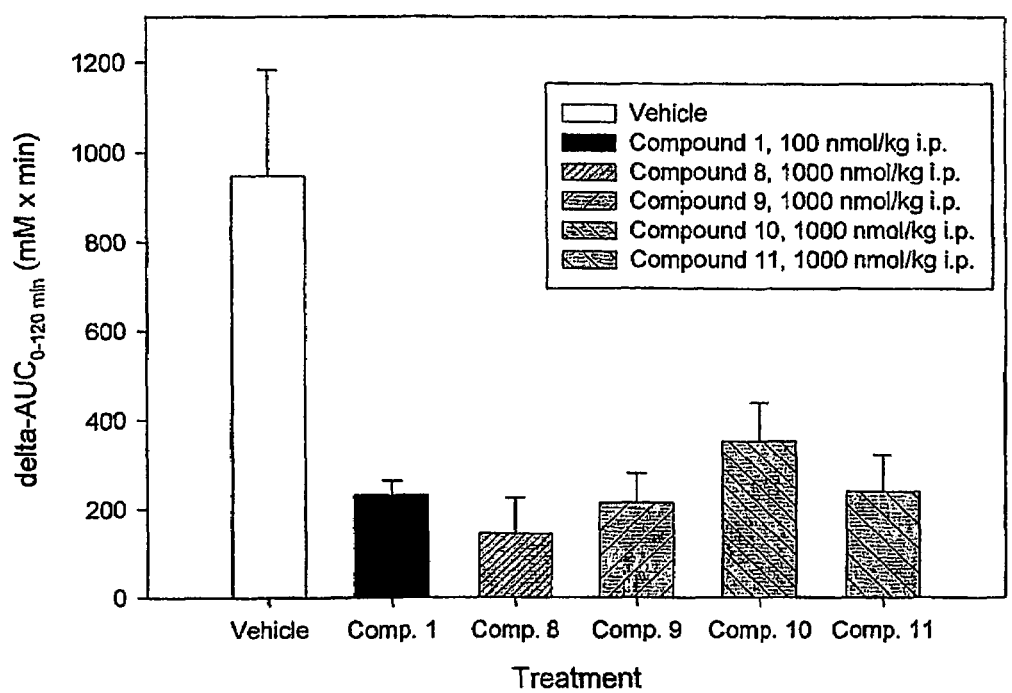
FIG. 8 depicts the influence of Compounds 1, 8, 9, 10 and 11 on blood glucose levels in mice.

In another set of experiments Compound 1, Compound 2 and Compound 5 were tested as described above. The results are illustrated in FIGS. 5, 6 and 7. The ED$_{50}$ values are outlined in Table 2.

TABLE 2

| Major Compound in Test Solution | ED$_{50}$ (nmol/kg) | SD$_r$ |
|---|---|---|
| Compound 1 | 0.073 | 4.1 |
| Compound 5 | 0.043 | 4.1 |
| Compound 2 | 0.011 | 36 |

ED$_{50}$ based on curve fits. The calculation of standard deviation ratio (SD$_r$) is presented above.

The fit of the data obtained after treatment with Compound 1 is illustrated in FIG. 5. The calculated ED$_{50}$ and SD$_r$ is shown in Table 2.

The fit of the data obtained after treatment with Compound 5 is illustrated in FIG. 6. The calculated ED$_{50}$ and SD$_r$ is shown in Table 2.

The fit of the data obtained after treatment with Compound 2 is illustrated in FIG. 7. The calculated ED$_{50}$, and SD$_r$ are shown in Table 1.

In conclusion, the above Compounds all showed anti diabetic effect by significantly increased glucose tolerance in the db/db mice as shown by a reduction in AUC$_{0-120\ min}$ or AUC$_{0-240\ min}$ (illustrated in the FIGS. 1-8). All the solutions tested had positive effect on glucose tolerance in doses above 0.01 nmol/kg. Thus, administration of the test compounds produced a dose-dependent lowering of blood glucose following a glucose load.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. Various references are cited herein, the disclosure of which are incorporated by reference in their entireties.

What is claimed is:

1. A composition comprising an exendin-4 (1-39) analog comprising a sequence selected from the group consisting of:
   [Asp$^{28}$]Exendin-4 (1-39) (SEQ ID NO:83),
   des Pro$^{36}$[Asp$^{28}$]Exendin-4 (1-39) (SEQ ID NO:15),
   des Pro$^{36}$, Pro$^{37}$[Asp$^{28}$]Exendin-4 (1-39) (SEQ ID NO:108), and
   des Pro$^{36}$, Pro$^{37}$, Pro$^{38}$[Asp$^{28}$]Exendin-4 (1-39) (SEQ ID NO:28).

2. The composition of claim 1 further comprising at least one peptide sequence Z of 4-20 amino acid residues covalently bound to the exendin analog; or a pharmaceutically acceptable salt or solvate thereof.

3. The composition of claim 2, wherein Z comprises between about 4 to about 20 Lys amino acid units.

4. The composition of claim 2, wherein Z comprises 6 Lys amino acid units.

5. The composition of claim 2, wherein the exendin-4 (1-39) analog and Z are bonded by a peptide bond.

6. The composition of claim 2, wherein Z is covalently bound to the exendin-4 (1-39) analog at the C-terminal carbonyl function.

7. A composition of claim 2, further comprising a pharmaceutically acceptable carrier.

8. The composition of claim 7, wherein the composition comprises a depot formulation, microspheres, liposomes or the composition includes a stabilized liquid formulation.

9. A method for treating disease states associated with elevated blood glucose levels, said method comprising administering a therapeutically effective amount of the composition of claim 2.

10. A method for regulation of blood glucose levels, the method comprising administering a therapeutically effective amount of the composition of claim 2.

11. A method of stimulating insulin release in a mammal comprising administering an effective insulinotropic amount of the composition of claim 2.

12. The composition of claim 1 further comprising the following group linked to the C-terminus of the analog: -Lys$_6$-NH$_2$.

13. The composition of claim 1, wherein the exendin-4 (1-39) analog comprises a sequence selected from the group consisting of:
   H-(Lys)$_6$-des Pro$^{36}$[Asp$^{28}$]Exendin-4 (1-39)-Lys$_6$-NH$_2$ (SEQ ID NO:27),
   H-(Lys)$_6$-des Pro$^{36}$, Pro$^{37}$, Pro$^{38}$[Asp$^{28}$]Exendin-4 (1-39)-NH$_2$ (SEQ ID NO:29),
   H-Asn-(Glu)$_5$des Pro$^{36}$, Pro$^{37}$, Pro$^{38}$[Asp$^{28}$]Exendin-4 (1-39)-NH$_2$ (SEQ ID NO:30),
   des Pro$^{36}$, Pro$^{37}$, Pro$^{38}$[Asp$^{28}$]Exendin-4 (1-39)-(Lys)$_6$-NH$_2$ (SEQ ID NO:31),
   H-(Lys)$_6$-des Pro$^{36}$, Pro$^{37}$, Pro$^{38}$[Asp$^{28}$]Exendin-4 (1-39)-(Lys)$_6$-NH$_2$ (SEQ ID NO:32), and
   H-Asn-(Glu)$_5$-des Pro$^{36}$, Pro$^{37}$, Pro$^{38}$[Asp$^{28}$]Exendin-4 (1-39)-(Lys)$_6$-NH$_2$ (SEQ ID NO:33),
   or a pharmaceutically acceptable salt or solvate thereof.

14. The composition of claim 13, said analog comprising the sequence H-(Lys)$_6$-des Pro$^{36}$[Asp$^{28}$]Exendin-4 (1-39)-Lys$_6$-NH$_2$ (SEQ ID NO:27).

15. The composition of claim 13, said analog comprising the sequence H-(Lys)$_6$-des Pro$^{36}$, Pro$^{37}$, Pro$^{38}$[Asp$^{28}$]Exendin-4 (1-39)-NH$_2$ (SEQ ID NO:29).

16. The composition of claim 13, said analog comprising the sequence H-Asn-(Glu)$_5$des Pro$^{36}$, Pro$^{37}$, Pro$^{38}$[Asp$^{28}$]Exendin-4 (1-39)-NH$_2$ (SEQ ID NO:30).

17. The composition of claim 13, said analog comprising the sequence des Pro$^{36}$, Pro$^{37}$, Pro$^{38}$[Asp$^{28}$]Exendin-4 (1-39)-(Lys)$_6$-NH$_2$ (SEQ ID NO:31).

18. The composition of claim 13, said analog comprising the sequence H-(Lys)$_6$-des Pro$^{36}$, Pro$^{37}$, Pro$^{38}$[Asp$^{28}$]Exendin-4 (1-39)-(Lys)$_6$-NH$_2$ (SEQ ID NO:32).

19. The composition of claim 13, said analog comprising the sequence H-Asn-(Glu)$_5$-des Pro$^{36}$, Pro$^{37}$, Pro$^{38}$[Asp$^{28}$]Exendin-4 (1-39)-(Lys)$_6$-NH$_2$ (SEQ ID NO:33).

20. The composition of claim 1, wherein the composition includes a mixture of L- and D-amino acid residues.

21. A composition of any one of claims 3-20, further comprising a pharmaceutically acceptable carrier.

22. The composition of claim 21, wherein the composition comprises a depot formulation, microspheres, or liposomes, or the composition includes a stabilized liquid formulation.

23. A method for treating diabetes type 1, the method comprising administering a therapeutically effective amount of the composition of claim 1.

24. A method for treating disease states associated with elevated blood glucose levels, said method comprising administering a therapeutically effective amount of the composition of claim 1.

25. A method for regulation of blood glucose levels, the method comprising administering a therapeutically effective amount of the composition of claim 1.

26. A method of stimulating insulin release in a mammal comprising administering an effective insulinotropic amount of the composition of claim 1.

27. The composition of claim 1, said sequence comprising [$Asp^{28}$]Exendin-4 (1-39) (SEQ ID NO:83).

28. The composition of claim 1, said sequence comprising des $Pro^{36}$[$Asp^{28}$]Exendin-4 (1-39) (SEQ ID NO:15).

29. The composition of claim 1, said analog comprising the sequence des $Pro^{36}$, $Pro^{37}$[$Asp^{28}$]Exendin-4 (1-39) (SEQ ID NO:108).

30. The composition of claim 1, said analog comprising the sequence des $Pro^{36}$, $Pro^{37}$, $Pro^{38}$[$Asp^{28}$]Exendin-4 (1-39) (SEQ ID NO:28).

31. The composition of claim 1, wherein the amino acid residues of said exendin-4 (1-39) analog are in the L configuration.

32. The composition of claim 1, wherein the amino acid residues of said exendin-4 (1-39) analog are in the D configuration.

\* \* \* \* \*

UNITED STATES PATENT AND TRADEMARK OFFICE
CERTIFICATE OF CORRECTION

PATENT NO. : 7,544,657 B2  Page 1 of 1
APPLICATION NO. : 10/529858
DATED : June 9, 2009
INVENTOR(S) : Ebbehoj et al.

It is certified that error appears in the above-identified patent and that said Letters Patent is hereby corrected as shown below:

On the Title Page

Item [*] Notice: Subject to any disclaimer, the term of this patent is extended or adjusted under 35 USC 154(b) by (34) days Delete the phrase "by 34 days" and insert -- by 299 days --

Signed and Sealed this

Twenty-ninth Day of December, 2009

David J. Kappos
*Director of the United States Patent and Trademark Office*